United States Patent
Gordon et al.

(10) Patent No.: US 11,421,208 B2
(45) Date of Patent: Aug. 23, 2022

(54) MATERIALS AND METHODS FOR INCREASING GENE EDITING FREQUENCY

(71) Applicant: Regents of the University of Minnesota, Minneapolis, MN (US)

(72) Inventors: Wendy R. Gordon, Minneapolis, MN (US); Eric Aird, Minneapolis, MN (US); Klaus Lovendahl, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 315 days.

(21) Appl. No.: 16/622,554

(22) PCT Filed: Jun. 13, 2018

(86) PCT No.: PCT/US2018/037353
§ 371 (c)(1),
(2) Date: Dec. 13, 2019

(87) PCT Pub. No.: WO2018/231999
PCT Pub. Date: Dec. 20, 2018

(65) Prior Publication Data
US 2020/0231952 A1 Jul. 23, 2020

Related U.S. Application Data

(60) Provisional application No. 62/518,960, filed on Jun. 13, 2017.

(51) Int. Cl.
*C12N 9/22* (2006.01)
*C12N 15/11* (2006.01)
*C12N 15/87* (2006.01)

(52) U.S. Cl.
CPC ............... *C12N 9/22* (2013.01); *C12N 15/11* (2013.01); *C12N 15/87* (2013.01); *C12N 2800/80* (2013.01)

(58) Field of Classification Search
None
See application file for complete search history.

(56) References Cited

U.S. PATENT DOCUMENTS

| | | |
|---|---|---|
| 2011/0145940 A1 | 6/2011 | Voytas et al. |
| 2015/0167000 A1 | 6/2015 | Voytas et al. |
| 2016/0340395 A1 | 11/2016 | Gordon et al. |
| 2017/0058298 A1 | 3/2017 | Kennedy et al. |
| 2019/0136210 A1 | 5/2019 | Cotta-Ramusino et al. |

OTHER PUBLICATIONS

Anders et al., "In vitro reconstitution and crystallization of Cas9 endonuclease bound to a guide RNA and a DNA target," Methods in Enzymology, 558:515-537, 2015.

Christian et al., "Targeting DNA double-strand breaks with TAL effector nucleases," Genetics, 186(2):757-761, Oct. 2010.
Cox et al., "Therapeutic genome editing: prospects and challenges," Nat. Med., 21(2):121-131, Feb. 2015.
Doudna et al., "The new frontier of genome engineering with CRISPR-Cas9," Science, 346(6213):1258096, Nov. 2014, 11 pages.
Gasiunas et al., "Cas9-crRNA ribonucleoprotein complex mediates specific DNA cleavage for adaptive immunity in bacteria," Proc. Nat. Acad. Sciences, 109(39):E2579-2586, Sep. 2012.
Jacoby et al., "Expanding LAGLIDADG endonuclease scaffold diversity by rapidly surveying evolutionary sequence space," Nucleic Acids Research, 40(11):4954-4964, Feb. 2012.
Jinek et al.. "A programmable dual-RNA-guided DNA endonuclease in adaptive bacterial immunity," Science, 337(6096):816-821, Aug. 17, 2012.
Livak et al., "Analysis of relative gene expression data using real-time quantitative PCR and the 2-ΔΔCT method," Methods, 25(4):402-408, Dec. 2001.
Lovendahl et al., "Sequence-directed covalent protein-DNA linkages in a single step using HUH-Tags," J. Am. Chem. Society, 139(20):7030-7035, May 8, 2017.
Mali et al., "CAS9 transcriptional activators for target specificity screening and paired nickases for cooperative genome engineering," Nat. Biotechnology, 31(9):833-838, Sep. 2013.
PCT International Preliminary Report on Patentability in International Appln. No. PCT/US2018/037353, dated Dec. 26, 2019, 8 pages.
PCT International Search Report & Written Opinion in International Appln. No. PCT/US2018/037353, dated Oct. 26, 2018, 12 pages.
Pinello et al., "Analyzing CRISPR genome-editing experiments with CRISPResso," Nat. Biotechnology, 34(7):695-697, Jul. 2016.
Qi et al., "Repurposing CRISPR as an RNA-Guided Platform for Sequence-Specific Control of Gene Expression," Cell, 152(5):1173-1183, Feb. 28, 2013.
Sander et al., "Selection-free zinc-finger-nuclease engineering by context-dependent assembly (CoDA)," Nat. Methods, 8(1):67-69, Jan. 2011.
Schwinn et al., "CRISPR-Mediated Tagging of Endogenous Proteins with a Luminescent Peptide," ACS Chem. Biology, 13(2):467-474, Sep. 11, 2017.
UniProt Accession No. Q03JI6, "CRISPR-associated endonuclease Cas9 2," May 11, 2016, 4 pages.

(Continued)

*Primary Examiner* — Suzanne M Noakes
*Assistant Examiner* — Jae W Lee
(74) *Attorney, Agent, or Firm* — Fish & Richardson P.C.

(57) ABSTRACT

Materials and methods for gene editing using improved targeted endonucleases and endonuclease systems (e.g., Clustered Regularly Interspaced Short Palindromic Repeats (CRISPR)/CRISPR-associated protein 9 (Cas9) endonuclease systems) are provided herein.

7 Claims, 12 Drawing Sheets
Specification includes a Sequence Listing.

(56) References Cited

OTHER PUBLICATIONS

UniProt Accession No. Q99ZW2, "CRISPR-associated endonuclease Cas9/Csn1," Jun. 8, 2016, 11 pages.
Zhang et al., "High frequency targeted mutagenesis in *Arabidopsis thaliana* using zinc finger nucleases," Proc. Nat. Acad. Sciences, 107(26):12028-12033, Jun. 29, 2010.
Zuris et al., "Cationic lipid-mediated delivery of proteins enables efficient protein-based genome editing in vitro and in vivo," Nat. Biotechnology, 33(1):73-80, Jan. 2015.

FIG. 6B

| DNA source | Target | $C_T$ | Average $C_T$ |
|---|---|---|---|
| Cas9 | GAPDH | 21.89 | 21.94±0.06 |
| | | 21.93 | |
| | | 22.00 | |
| | HiBiT | 25.77 | 25.32±0.60 |
| | | 25.54 | |
| | | 24.64 | |
| Cas9-PCV | GAPDH | 22.17 | 22.07±0.09 |
| | | 22.00 | |
| | | 22.05 | |
| | HiBiT | 24.52 | 24.46±0.10 |
| | | 24.52 | |
| | | 24.34 | |
| Change in HDR with Cas9-PCV: 1.98 fold* | | | |

* Ratio calculated using Pfaffl Method where *GAPDH* is the reference

SEQUENCE LISTING

<160> NUMBER OF SEQ ID NOS: 24

<210> SEQ ID NO 1
<211> LENGTH: 116
<212> TYPE: PRT
<213> ORGANISM: Porcine circovirus 2

<400> SEQUENCE: 1

Ser Pro Ser Lys Lys Asn Gly Arg Ser Gly Pro Gln Pro His Lys Arg
1               5                   10                  15

Trp Val Phe Thr Leu Asn Asn Pro Ser Glu Asp Glu Arg Lys Lys Ile
            20                  25                  30

Arg Asp Leu Pro Ile Ser Leu Phe Asp Tyr Phe Ile Val Gly Glu Glu
        35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Leu Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Met Glu Cys Gly Ala Pro Arg Ser
            100                 105                 110

Gln Gly Gln Arg
        115

<210> SEQ ID NO 2
<211> LENGTH: 340
<212> TYPE: PRT
<213> ORGANISM: Bacteriophage PhiX174

<400> SEQUENCE: 2

Lys Ser Arg Arg Gly Phe Ala Ile Gln Arg Leu Met Asn Ala Met Arg
1               5                   10                  15

Gln Ala His Ala Asp Gly Trp Phe Ile Val Phe Asp Thr Leu Thr Leu
            20                  25                  30

Ala Asp Asp Arg Leu Glu Ala Phe Tyr Asp Asn Pro Asn Ala Leu Arg
        35                  40                  45

Asp Tyr Phe Arg Asp Ile Gly Arg Met Val Leu Ala Ala Glu Gly Arg
    50                  55                  60

Lys Ala Asn Asp Ser His Ala Asp Cys Tyr Gln Tyr Phe Cys Val Pro
65                  70                  75                  80

Glu Tyr Gly Thr Ala Asn Gly Arg Leu His Phe His Ala Val His Phe
                85                  90                  95

Met Arg Thr Leu Pro Thr Gly Ser Val Asp Pro Asn Phe Gly Arg Arg
            100                 105                 110

Val Arg Asn Arg Arg Gln Leu Asn Ser Leu Gln Asn Thr Trp Pro Tyr
        115                 120                 125

Gly His Ser Met Pro Ile Ala Val Arg Tyr Thr Gln Asp Ala Phe Ser
    130                 135                 140

Arg Ser Gly Trp Leu Trp Pro Val Asp Ala Lys Gly Glu Pro Leu Lys
145                 150                 155                 160

Ala Thr Ser Tyr Met Ala Val Gly Phe Tyr Val Ala Lys Tyr Val Asn
                165                 170                 175

Lys Lys Ser Asp Met Asp Leu Ala Ala Lys Gly Leu Gly Ala Lys Glu
            180                 185                 190

Trp Asn Asn Ser Leu Lys Thr Lys Leu Ser Leu Leu Pro Lys Lys Leu

```
            195                 200                 205

Phe Arg Ile Arg Met Ser Arg Asn Phe Gly Met Lys Met Leu Thr Met
210                 215                 220

Thr Asn Leu Ser Thr Glu Cys Leu Ile Gln Leu Thr Lys Leu Gly Tyr
225                 230                 235                 240

Asp Ala Thr Pro Phe Asn Gln Ile Leu Lys Gln Asn Ala Lys Arg Glu
                245                 250                 255

Met Arg Leu Arg Leu Gly Lys Val Thr Val Ala Asp Val Leu Ala Ala
            260                 265                 270

Gln Pro Val Thr Thr Asn Leu Leu Lys Phe Met Arg Ala Ser Ile Lys
        275                 280                 285

Met Ile Gly Val Ser Asn Leu Gln Ser Phe Ile Ala Ser Met Thr Gln
    290                 295                 300

Lys Leu Thr Leu Ser Asp Ile Ser Asp Glu Ser Lys Asn Tyr Leu Asp
305                 310                 315                 320

Lys Ala Gly Ile Thr Thr Ala Cys Leu Arg Ile Lys Ser Lys Trp Thr
                325                 330                 335

Ala Gly Gly Lys
            340

<210> SEQ ID NO 3
<211> LENGTH: 186
<212> TYPE: PRT
<213> ORGANISM: Escherichia coli

<400> SEQUENCE: 3

Met Ala Ile Tyr His Leu Thr Ala Lys Thr Gly Ser Arg Ser Gly Gly
1               5                   10                  15

Gln Ser Ala Arg Ala Lys Ala Asp Tyr Ile Gln Arg Glu Gly Lys Tyr
            20                  25                  30

Ala Arg Asp Met Asp Glu Val Leu His Ala Glu Ser Gly His Met Pro
        35                  40                  45

Glu Phe Val Glu Arg Pro Ala Asp Tyr Trp Asp Ala Ala Asp Leu Tyr
    50                  55                  60

Glu Arg Ala Asn Gly Arg Leu Phe Lys Glu Val Glu Phe Ala Leu Pro
65                  70                  75                  80

Val Glu Leu Thr Leu Asp Gln Gln Lys Ala Leu Ala Ser Glu Phe Ala
                85                  90                  95

Gln His Leu Thr Gly Ala Glu Arg Leu Pro Tyr Thr Leu Ala Ile His
            100                 105                 110

Ala Gly Gly Gly Glu Asn Pro His Cys His Leu Met Ile Ser Glu Arg
        115                 120                 125

Ile Asn Asp Gly Ile Glu Arg Pro Ala Ala Gln Trp Phe Lys Arg Tyr
    130                 135                 140

Asn Gly Lys Thr Pro Glu Lys Gly Gly Ala Gln Lys Thr Glu Ala Leu
145                 150                 155                 160

Lys Pro Lys Ala Trp Leu Glu Gln Thr Arg Glu Ala Trp Ala Asp His
                165                 170                 175

Ala Asn Arg Ala Leu Glu Arg Ala Gly His
            180                 185

<210> SEQ ID NO 4
<211> LENGTH: 330
<212> TYPE: PRT
<213> ORGANISM: Escherichia coli
```

<400> SEQUENCE: 4

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Arg Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Arg His Arg Pro Gly Tyr
65                  70                  75                  80

Asp Leu Thr Phe Ser Ala Pro Lys Ser Val Ser Met Met Ala Met Leu
            85                  90                  95

Gly Gly Asp Lys Arg Leu Ile Asp Ala His Asn Gln Ala Val Asp Phe
        100                 105                 110

Ala Val Arg Gln Val Glu Ala Leu Ala Ser Thr Arg Val Met Thr Asp
    115                 120                 125

Gly Gln Ser Glu Thr Val Leu Thr Gly Asn Leu Val Met Ala Leu Phe
130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
            165                 170                 175

Ser Asp Lys Val Gly Lys Thr Gly Phe Ile Glu Asn Val Tyr Ala Asn
        180                 185                 190

Gln Ile Ala Phe Gly Arg Leu Tyr Arg Glu Lys Leu Lys Glu Gln Val
    195                 200                 205

Glu Ala Leu Gly Tyr Glu Thr Glu Val Val Gly Lys His Gly Met Trp
210                 215                 220

Glu Met Pro Gly Val Pro Val Glu Ala Phe Ser Gly Arg Ser Gln Thr
225                 230                 235                 240

Ile Arg Glu Ala Val Gly Glu Asp Ala Ser Leu Lys Ser Arg Asp Val
            245                 250                 255

Ala Ala Leu Asp Thr Arg Lys Ser Lys Gln His Val Asp Pro Glu Ile
        260                 265                 270

Lys Met Ala Glu Trp Met Gln Thr Leu Lys Glu Thr Gly Phe Asp Ile
    275                 280                 285

Arg Ala Tyr Arg Asp Ala Ala Asp Gln Arg Ala Asp Leu Arg Thr Leu
290                 295                 300

Thr Pro Gly Pro Ala Ser Gln Asp Gly Pro Asp Val Gln Gln Ala Val
305                 310                 315                 320

Thr Gln Ala Ile Ala Gly Leu Ser Glu Arg
            325                 330

<210> SEQ ID NO 5
<211> LENGTH: 133
<212> TYPE: PRT
<213> ORGANISM: Streptococcus agalactiae

<400> SEQUENCE: 5

Met Ala Lys Glu Lys Ala Arg Tyr Phe Thr Phe Leu Leu Tyr Pro Glu
1               5                   10                  15

Ser Ile Pro Ser Asp Trp Glu Leu Lys Leu Glu Thr Leu Gly Val Pro
            20                  25                  30

```
Met Ala Ile Ser Pro Leu His Asp Lys Asp Lys Ser Ser Ile Lys Gly
        35                  40                  45

Gln Lys Tyr Lys Lys Ala His Tyr His Val Leu Tyr Ile Ala Lys Asn
    50                  55                  60

Pro Val Thr Ala Asp Ser Val Arg Lys Lys Ile Lys Leu Leu Leu Gly
65                  70                  75                  80

Glu Lys Ser Leu Ala Met Val Gln Val Val Leu Asn Val Glu Asn Met
                85                  90                  95

Tyr Leu Tyr Leu Thr His Glu Ser Lys Asp Ala Ile Ala Lys Lys Lys
            100                 105                 110

His Val Tyr Asp Lys Ala Asp Ile Lys Leu Ile Asn Asn Phe Asp Ile
        115                 120                 125

Asp Arg Tyr Leu Glu
    130

<210> SEQ ID NO 6
<211> LENGTH: 130
<212> TYPE: PRT
<213> ORGANISM: Streptococcus pneumonia

<400> SEQUENCE: 6

Met Ser Glu Lys Lys Glu Ile Val Lys Gly Arg Asp Trp Thr Phe Leu
1               5                   10                  15

Val Tyr Pro Glu Ser Ala Pro Glu Asn Trp Arg Thr Ile Leu Asp Glu
            20                  25                  30

Thr Phe Met Arg Trp Val Glu Ser Pro Leu His Asp Lys Asp Val Asn
        35                  40                  45

Ala Asp Gly Glu Ile Lys Lys Pro His Trp His Ile Leu Leu Ser Ser
    50                  55                  60

Asp Gly Pro Ile Thr Gln Thr Ala Val Gln Lys Ile Ile Gly Pro Leu
65                  70                  75                  80

Asn Cys Pro Asn Ala Gln Lys Val Gly Ser Ala Lys Gly Leu Val Arg
                85                  90                  95

Tyr Met Val His Leu Asp Asn Pro Glu Lys Tyr Gln Tyr Ser Leu Asp
            100                 105                 110

Glu Ile Val Gly His Asn Gly Ala Asp Val Ala Ser Tyr Phe Glu Leu
        115                 120                 125

Thr Ala
    130

<210> SEQ ID NO 7
<211> LENGTH: 98
<212> TYPE: PRT
<213> ORGANISM: Fava bean necrotic yellow virus

<400> SEQUENCE: 7

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
            20                  25                  30

Glu Gln Gly Glu Ala Gly Asn Ile His Phe Gln Gly Tyr Ile Glu Met
        35                  40                  45

Lys Lys Arg Thr Ser Leu Ala Gly Met Lys Lys Leu Ile Pro Gly Ala
    50                  55                  60

His Phe Glu Lys Arg Arg Gly Thr Gln Gly Glu Ala Arg Ala Tyr Ser
65                  70                  75                  80
```

```
Met Lys Glu Asp Thr Arg Leu Glu Gly Pro Trp Glu Tyr Gly Glu Phe
                85                  90                  95

Val Pro
```

<210> SEQ ID NO 8
<211> LENGTH: 219
<212> TYPE: PRT
<213> ORGANISM: Staphylococcus aureus

<400> SEQUENCE: 8

```
Ala Met Tyr His Phe Gln Asn Lys Phe Val Ser Lys Ala Asn Gly Gln
1               5                   10                  15

Ser Ala Thr Ala Lys Ser Ala Tyr Asn Ser Ala Ser Arg Ile Lys Asp
                20                  25                  30

Phe Lys Glu Asn Glu Phe Lys Asp Tyr Ser Asn Lys Gln Cys Asp Tyr
                35                  40                  45

Ser Glu Ile Leu Leu Pro Asn Asn Ala Asp Asp Lys Phe Lys Asp Arg
                50                  55                  60

Glu Tyr Leu Trp Asn Lys Val His Asp Val Glu Asn Arg Lys Asn Ser
65              70                  75                  80

Gln Val Ala Arg Glu Ile Ile Ile Gly Leu Pro Asn Glu Phe Asp Pro
                85                  90                  95

Asn Ser Asn Ile Glu Leu Ala Lys Glu Phe Ala Glu Ser Leu Ser Asn
                100                 105                 110

Glu Gly Met Ile Val Asp Leu Asn Ile His Lys Ile Asn Glu Glu Asn
                115                 120                 125

Pro His Ala His Leu Leu Cys Thr Leu Arg Gly Leu Asp Lys Asn Asn
                130                 135                 140

Glu Phe Glu Pro Lys Arg Lys Gly Asn Asp Tyr Ile Arg Asp Trp Asn
145                 150                 155                 160

Thr Lys Glu Lys His Asn Glu Trp Arg Lys Arg Trp Glu Asn Val Gln
                165                 170                 175

Asn Lys His Leu Glu Lys Asn Gly Phe Ser Val Arg Val Ser Ala Asp
                180                 185                 190

Ser Tyr Lys Asn Gln Asn Ile Asp Leu Glu Pro Thr Lys Lys Glu Gly
                195                 200                 205

Trp Lys Ala Arg Lys Phe Glu Asp Glu Thr Gly
    210                 215
```

<210> SEQ ID NO 9
<211> LENGTH: 293
<212> TYPE: PRT
<213> ORGANISM: Escherichia coli

<400> SEQUENCE: 9

```
Met Leu Ser His Met Val Leu Thr Arg Gln Asp Ile Gly Arg Ala Ala
1               5                   10                  15

Ser Tyr Tyr Glu Asp Gly Ala Asp Tyr Tyr Ala Lys Asp Gly Asp
                20                  25                  30

Ala Ser Glu Trp Gln Gly Lys Gly Ala Glu Glu Leu Gly Leu Ser Gly
                35                  40                  45

Glu Val Asp Ser Lys Arg Phe Arg Glu Leu Leu Ala Gly Asn Ile Gly
                50                  55                  60

Glu Gly His Arg Ile Met Arg Ser Ala Thr Arg Gln Asp Ser Lys Glu
65              70                  75                  80

Arg Ile Gly Leu Asp Leu Thr Phe Ser Ala Pro Lys Ser Val Ser Leu
```

```
            85                  90                  95
Gln Ala Leu Val Ala Gly Asp Ala Glu Ile Ile Lys Ala His Asp Arg
            100                 105                 110

Ala Val Ala Arg Thr Leu Glu Gln Ala Glu Arg Ala Gln Ala Arg
        115                 120                 125

Gln Lys Ile Gln Gly Lys Thr Arg Ile Glu Thr Thr Gly Asn Leu Val
        130                 135                 140

Ile Gly Lys Phe Arg His Glu Thr Ser Arg Glu Arg Asp Pro Gln Leu
145                 150                 155                 160

His Thr His Ala Val Ile Leu Asn Met Thr Lys Arg Ser Asp Gly Gln
                165                 170                 175

Trp Arg Ala Leu Lys Asn Asp Glu Ile Val Lys Ala Thr Arg Tyr Leu
                180                 185                 190

Gly Ala Val Tyr Asn Ala Glu Leu Ala His Glu Leu Gln Lys Leu Gly
            195                 200                 205

Tyr Gln Leu Arg Tyr Gly Lys Asp Gly Asn Phe Asp Leu Ala His Ile
        210                 215                 220

Asp Arg Gln Gln Ile Glu Gly Phe Ser Lys Arg Thr Glu Gln Ile Ala
225                 230                 235                 240

Glu Trp Tyr Ala Ala Arg Gly Leu Asp Pro Asn Ser Val Ser Leu Glu
                245                 250                 255

Gln Lys Gln Ala Ala Lys Val Leu Ser Arg Ala Lys Lys Thr Ser Val
                260                 265                 270

Asp Arg Glu Ala Leu Arg Ala Glu Trp Gln Ala Thr Ala Lys Glu Leu
        275                 280                 285

Gly Ile Asp Phe Ser
        290

<210> SEQ ID NO 10
<211> LENGTH: 257
<212> TYPE: PRT
<213> ORGANISM: Agrobacterium tumefaciens

<400> SEQUENCE: 10

Met Pro Asp Arg Ala Gln Val Ile Ile Arg Ile Val Pro Gly Gly Gly
1               5                   10                  15

Thr Lys Thr Leu Gln Gln Ile Ile Asn Gln Leu Glu Tyr Leu Ser Arg
            20                  25                  30

Lys Gly Arg Leu Glu Leu Gln Arg Ser Ala Arg His Leu Asp Ile Pro
        35                  40                  45

Leu Pro Pro Asp Gln Ile His Glu Leu Ala Arg Ser Trp Val Gln Glu
    50                  55                  60

Thr Gly Thr Tyr Asp Glu Ser Gln Pro Asp Glu Glu Arg Gln Gln Glu
65                  70                  75                  80

Leu Thr Thr His Ile Ile Val Ser Phe Pro Ala Gly Thr Ser Gln Val
                85                  90                  95

Ala Ala Tyr Ala Ala Ser Arg Glu Trp Ala Ala Glu Met Phe Gly Ser
            100                 105                 110

Gly Ala Gly Gly Gly Arg Tyr Asn Tyr Leu Thr Ala Phe His Ile Asp
        115                 120                 125

Arg Asp His Pro His Leu His Val Val Asn Arg Glu Leu Leu
    130                 135                 140

Gly His Gly Trp Leu Lys Ile Ser Arg Arg His Pro Gln Leu Asn Tyr
145                 150                 155                 160
```

```
Asp Ala Leu Arg Ile Lys Met Ala Glu Ile Ser Leu Arg His Gly Ile
            165                 170                 175
Ala Leu Asp Ala Ser Arg Arg Ala Glu Arg Gly Ile Thr Glu Arg Pro
        180                 185                 190
Ile Thr Tyr Ala Gln Tyr Arg Arg Leu Glu Arg Glu Gln Ala Arg Gln
            195                 200                 205
Ile Arg Phe Glu Asp Ala Asp Leu Glu Gln Ser Ser Pro Gln Gly Asp
        210                 215                 220
His Pro Glu Phe Ser Gln Pro Phe Asp Thr Ser Pro Phe Glu Ala Ser
225                 230                 235                 240
Ala Gly Gly Pro Glu Asp Met Pro Arg Pro Asn Asn Arg Gln Asn Glu
            245                 250                 255
Ser

<210> SEQ ID NO 11
<211> LENGTH: 120
<212> TYPE: PRT
<213> ORGANISM: Tomato yellow leaf curl virus

<400> SEQUENCE: 11

Met Pro Arg Leu Phe Lys Ile Tyr Ala Lys Asn Tyr Phe Leu Thr Tyr
1               5                   10                  15
Pro Asn Cys Ser Leu Ser Lys Glu Glu Ala Leu Ser Gln Leu Lys Lys
            20                  25                  30
Leu Glu Thr Pro Thr Asn Lys Lys Tyr Ile Lys Val Cys Lys Glu Leu
        35                  40                  45
His Glu Asn Gly Glu Pro His Leu His Val Leu Ile Gln Phe Glu Gly
    50                  55                  60
Lys Tyr Gln Cys Lys Asn Gln Arg Phe Phe Asp Leu Val Ser Pro Asn
65                  70                  75                  80
Arg Ser Ala His Phe His Pro Asn Ile Gln Ala Ala Lys Ser Ser Thr
                85                  90                  95
Asp Val Lys Thr Tyr Val Glu Lys Asp Gly Asn Phe Ile Asp Phe Gly
            100                 105                 110
Val Ser Gln Ile Asp Gly Arg Ser
        115                 120

<210> SEQ ID NO 12
<211> LENGTH: 130
<212> TYPE: PRT
<213> ORGANISM: Streptococcus pneumoniae

<400> SEQUENCE: 12

Met Ser Glu Lys Lys Glu Ile Val Lys Gly Arg Asp Trp Thr Phe Leu
1               5                   10                  15
Val Tyr Pro Glu Ser Ala Pro Glu Asn Trp Arg Thr Ile Leu Asp Glu
            20                  25                  30
Thr Phe Met Arg Trp Val Glu Ser Pro Leu His Asp Lys Asp Val Asn
        35                  40                  45
Ala Asp Gly Glu Ile Lys Lys Pro His Trp His Ile Leu Leu Ser Ser
    50                  55                  60
Asp Gly Pro Ile Thr Gln Thr Ala Val Gln Lys Ile Ile Gly Pro Leu
65                  70                  75                  80
Asn Cys Pro Asn Ala Gln Lys Val Gly Ser Ala Lys Gly Leu Val Arg
                85                  90                  95
Tyr Met Val His Leu Asp Asn Pro Glu Lys Tyr Gln Tyr Ser Leu Asp
```

```
              100                 105                 110
Glu Ile Val Gly His Asn Gly Ala Asp Val Ala Ser Tyr Phe Glu Leu
            115                 120                 125

Thr Ala
    130

<210> SEQ ID NO 13
<211> LENGTH: 111
<212> TYPE: PRT
<213> ORGANISM: Duck circovirus

<400> SEQUENCE: 13

Met Ala Lys Ser Gly Asn Tyr Ser Tyr Lys Arg Trp Val Phe Thr Ile
1               5                  10                  15

Asn Asn Pro Thr Phe Glu Asp Tyr Val His Val Leu Glu Phe Cys Thr
            20                  25                  30

Leu Asp Asn Cys Lys Phe Ala Ile Val Gly Glu Glu Lys Gly Ala Asn
        35                  40                  45

Gly Thr Pro His Leu Gln Gly Phe Leu Asn Leu Arg Ser Asn Ala Arg
    50                  55                  60

Ala Ala Ala Leu Glu Glu Ser Leu Gly Gly Arg Ala Trp Leu Ser Arg
65                  70                  75                  80

Ala Arg Gly Ser Asp Glu Asp Asn Glu Glu Tyr Cys Ala Lys Glu Ser
                85                  90                  95

Thr Tyr Leu Arg Val Gly Glu Pro Val Ser Lys Gly Arg Ser Ser
            100                 105                 110

<210> SEQ ID NO 14
<211> LENGTH: 1388
<212> TYPE: PRT
<213> ORGANISM: Streptococcus thermophilus

<400> SEQUENCE: 14

Met Thr Lys Pro Tyr Ser Ile Gly Leu Asp Ile Gly Thr Asn Ser Val
1               5                  10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
```

-continued

```
                180                 185                 190
Asn Ala Ile Phe Glu Ser Asp Leu Ser Leu Glu Asn Ser Lys Gln Leu
            195                 200                 205

Glu Glu Ile Val Lys Asp Lys Ile Ser Lys Leu Glu Lys Lys Asp Arg
            210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Tyr Ser Asp
            275                 280                 285

Val Phe Leu Lys Ala Lys Lys Leu Tyr Asp Ala Ile Leu Leu Ser Gly
            290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
                340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Glu Phe Glu
            370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
                420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
            450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
            530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
            595                 600                 605
```

```
Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
                660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
        690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
                740                 745                 750

Gly Gly Arg Lys Pro Glu Ser Ile Val Val Glu Met Ala Arg Glu Asn
        755                 760                 765

Gln Tyr Thr Asn Gln Gly Lys Ser Asn Ser Gln Gln Arg Leu Lys Arg
    770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
                820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
                900                 905                 910

Gly Gly Leu Ser Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
                980                 985                 990

Asp Ala Tyr Leu Asn Ala Val Val Ala Ser Ala Leu Leu Lys Lys Tyr
        995                 1000                1005

Pro Lys Leu Glu Pro Glu Phe Val Tyr Gly Asp Tyr Pro Lys Tyr
    1010                1015                1020
```

Asn Ser Phe Arg Glu Arg Lys Ser Ala Thr Glu Lys Val Tyr Phe
1025                1030                1035

Tyr Ser Asn Ile Met Asn Ile Phe Lys Lys Ser Ile Ser Leu Ala
1040                1045                1050

Asp Gly Arg Val Ile Glu Arg Pro Leu Ile Glu Val Asn Glu Glu
1055                1060                1065

Thr Gly Glu Ser Val Trp Asn Lys Glu Ser Asp Leu Ala Thr Val
1070                1075                1080

Arg Arg Val Leu Ser Tyr Pro Gln Val Asn Val Val Lys Lys Val
1085                1090                1095

Glu Glu Gln Asn His Gly Leu Asp Arg Gly Lys Pro Lys Gly Leu
1100                1105                1110

Phe Asn Ala Asn Leu Ser Ser Lys Pro Lys Pro Asn Ser Asn Glu
1115                1120                1125

Asn Leu Val Gly Ala Lys Glu Tyr Leu Asp Pro Lys Lys Tyr Gly
1130                1135                1140

Gly Tyr Ala Gly Ile Ser Asn Ser Phe Thr Val Leu Val Lys Gly
1145                1150                1155

Thr Ile Glu Lys Gly Ala Lys Lys Lys Ile Thr Asn Val Leu Glu
1160                1165                1170

Phe Gln Gly Ile Ser Ile Leu Asp Arg Ile Asn Tyr Arg Lys Asp
1175                1180                1185

Lys Leu Asn Phe Leu Leu Glu Lys Gly Tyr Lys Asp Ile Glu Leu
1190                1195                1200

Ile Ile Glu Leu Pro Lys Tyr Ser Leu Phe Glu Leu Ser Asp Gly
1205                1210                1215

Ser Arg Arg Met Leu Ala Ser Ile Leu Ser Thr Asn Asn Lys Arg
1220                1225                1230

Gly Glu Ile His Lys Gly Asn Gln Ile Phe Leu Ser Gln Lys Phe
1235                1240                1245

Val Lys Leu Leu Tyr His Ala Lys Arg Ile Ser Asn Thr Ile Asn
1250                1255                1260

Glu Asn His Arg Lys Tyr Val Glu Asn His Lys Lys Glu Phe Glu
1265                1270                1275

Glu Leu Phe Tyr Tyr Ile Leu Glu Phe Asn Glu Asn Tyr Val Gly
1280                1285                1290

Ala Lys Lys Asn Gly Lys Leu Leu Asn Ser Ala Phe Gln Ser Trp
1295                1300                1305

Gln Asn His Ser Ile Asp Glu Leu Cys Ser Ser Phe Ile Gly Pro
1310                1315                1320

Thr Gly Ser Glu Arg Lys Gly Leu Phe Glu Leu Thr Ser Arg Gly
1325                1330                1335

Ser Ala Ala Asp Phe Glu Phe Leu Gly Val Lys Ile Pro Arg Tyr
1340                1345                1350

Arg Asp Tyr Thr Pro Ser Ser Leu Leu Lys Asp Ala Thr Leu Ile
1355                1360                1365

His Gln Ser Val Thr Gly Leu Tyr Glu Thr Arg Ile Asp Leu Ala
1370                1375                1380

Lys Leu Gly Glu Gly
1385

<210> SEQ ID NO 15
<211> LENGTH: 1368
<212> TYPE: PRT

<213> ORGANISM: Streptococcus pyogenes

<400> SEQUENCE: 15

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

-continued

```
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
```

-continued

```
              820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
```

```
Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 16
<211> LENGTH: 1616
<212> TYPE: PRT
<213> ORGANISM: Artificial Sequence
<220> FEATURE:
<223> OTHER INFORMATION: synthetic polypeptide

<400> SEQUENCE: 16

Met Arg Gly Ser His His His His His His Met Ala Ser Gly Ser Asp
1               5                   10                  15

Ser Glu Val Asn Gln Glu Ala Lys Pro Glu Val Lys Pro Glu Val Lys
                20                  25                  30

Pro Glu Thr His Ile Asn Leu Lys Val Ser Asp Gly Ser Ser Glu Ile
            35                  40                  45

Phe Phe Lys Ile Lys Lys Thr Thr Pro Leu Arg Arg Leu Met Glu Ala
50                  55                  60

Phe Ala Lys Arg Gln Gly Lys Glu Met Asp Ser Leu Arg Phe Leu Tyr
65                  70                  75                  80

Asp Gly Ile Arg Ile Gln Ala Asp Gln Thr Pro Glu Asp Leu Asp Met
                85                  90                  95

Glu Asp Asn Asp Ile Ile Glu Ala His Arg Glu Gln Ile Gly Gly Ser
            100                 105                 110

Met Asp Lys Lys Tyr Ser Ile Gly Leu Asp Ile Gly Thr Asn Ser Val
        115                 120                 125

Gly Trp Ala Val Ile Thr Asp Glu Tyr Lys Val Pro Ser Lys Lys Phe
    130                 135                 140

Lys Val Leu Gly Asn Thr Asp Arg His Ser Ile Lys Lys Asn Leu Ile
145                 150                 155                 160

Gly Ala Leu Leu Phe Asp Ser Gly Glu Thr Ala Glu Ala Thr Arg Leu
                165                 170                 175

Lys Arg Thr Ala Arg Arg Arg Tyr Thr Arg Arg Lys Asn Arg Ile Cys
            180                 185                 190

Tyr Leu Gln Glu Ile Phe Ser Asn Glu Met Ala Lys Val Asp Asp Ser
        195                 200                 205

Phe Phe His Arg Leu Glu Glu Ser Phe Leu Val Glu Glu Asp Lys Lys
    210                 215                 220
```

His Glu Arg His Pro Ile Phe Gly Asn Ile Val Asp Glu Val Ala Tyr
225                 230                 235                 240

His Glu Lys Tyr Pro Thr Ile Tyr His Leu Arg Lys Lys Leu Val Asp
            245                 250                 255

Ser Thr Asp Lys Ala Asp Leu Arg Leu Ile Tyr Leu Ala Leu Ala His
        260                 265                 270

Met Ile Lys Phe Arg Gly His Phe Leu Ile Glu Gly Asp Leu Asn Pro
    275                 280                 285

Asp Asn Ser Asp Val Asp Lys Leu Phe Ile Gln Leu Val Gln Thr Tyr
290                 295                 300

Asn Gln Leu Phe Glu Glu Asn Pro Ile Asn Ala Ser Gly Val Asp Ala
305                 310                 315                 320

Lys Ala Ile Leu Ser Ala Arg Leu Ser Lys Ser Arg Arg Leu Glu Asn
                325                 330                 335

Leu Ile Ala Gln Leu Pro Gly Glu Lys Lys Asn Gly Leu Phe Gly Asn
            340                 345                 350

Leu Ile Ala Leu Ser Leu Gly Leu Thr Pro Asn Phe Lys Ser Asn Phe
        355                 360                 365

Asp Leu Ala Glu Asp Ala Lys Leu Gln Leu Ser Lys Asp Thr Tyr Asp
    370                 375                 380

Asp Asp Leu Asp Asn Leu Leu Ala Gln Ile Gly Asp Gln Tyr Ala Asp
385                 390                 395                 400

Leu Phe Leu Ala Ala Lys Asn Leu Ser Asp Ala Ile Leu Leu Ser Asp
                405                 410                 415

Ile Leu Arg Val Asn Thr Glu Ile Thr Lys Ala Pro Leu Ser Ala Ser
            420                 425                 430

Met Ile Lys Arg Tyr Asp Glu His His Gln Asp Leu Thr Leu Leu Lys
        435                 440                 445

Ala Leu Val Arg Gln Gln Leu Pro Glu Lys Tyr Lys Glu Ile Phe Phe
    450                 455                 460

Asp Gln Ser Lys Asn Gly Tyr Ala Gly Tyr Ile Asp Gly Gly Ala Ser
465                 470                 475                 480

Gln Glu Glu Phe Tyr Lys Phe Ile Lys Pro Ile Leu Glu Lys Met Asp
                485                 490                 495

Gly Thr Glu Glu Leu Leu Val Lys Leu Asn Arg Glu Asp Leu Leu Arg
            500                 505                 510

Lys Gln Arg Thr Phe Asp Asn Gly Ser Ile Pro His Gln Ile His Leu
        515                 520                 525

Gly Glu Leu His Ala Ile Leu Arg Arg Gln Glu Asp Phe Tyr Pro Phe
    530                 535                 540

Leu Lys Asp Asn Arg Glu Lys Ile Glu Lys Ile Leu Thr Phe Arg Ile
545                 550                 555                 560

Pro Tyr Tyr Val Gly Pro Leu Ala Arg Gly Asn Ser Arg Phe Ala Trp
                565                 570                 575

Met Thr Arg Lys Ser Glu Glu Thr Ile Thr Pro Trp Asn Phe Glu Glu
            580                 585                 590

Val Val Asp Lys Gly Ala Ser Ala Gln Ser Phe Ile Glu Arg Met Thr
        595                 600                 605

Asn Phe Asp Lys Asn Leu Pro Asn Glu Lys Val Leu Pro Lys His Ser
    610                 615                 620

Leu Leu Tyr Glu Tyr Phe Thr Val Tyr Asn Glu Leu Thr Lys Val Lys
625                 630                 635                 640

-continued

```
Tyr Val Thr Glu Gly Met Arg Lys Pro Ala Phe Leu Ser Gly Glu Gln
            645                 650                 655
Lys Lys Ala Ile Val Asp Leu Leu Phe Lys Thr Asn Arg Lys Val Thr
            660                 665                 670
Val Lys Gln Leu Lys Glu Asp Tyr Phe Lys Lys Ile Glu Cys Phe Asp
            675                 680                 685
Ser Val Glu Ile Ser Gly Val Glu Asp Arg Phe Asn Ala Ser Leu Gly
            690                 695                 700
Thr Tyr His Asp Leu Leu Lys Ile Ile Lys Asp Lys Asp Phe Leu Asp
705                 710                 715                 720
Asn Glu Glu Asn Glu Asp Ile Leu Glu Asp Ile Val Leu Thr Leu Thr
                    725                 730                 735
Leu Phe Glu Asp Arg Glu Met Ile Glu Glu Arg Leu Lys Thr Tyr Ala
                740                 745                 750
His Leu Phe Asp Asp Lys Val Met Lys Gln Leu Lys Arg Arg Arg Tyr
            755                 760                 765
Thr Gly Trp Gly Arg Leu Ser Arg Lys Leu Ile Asn Gly Ile Arg Asp
            770                 775                 780
Lys Gln Ser Gly Lys Thr Ile Leu Asp Phe Leu Lys Ser Asp Gly Phe
785                 790                 795                 800
Ala Asn Arg Asn Phe Met Gln Leu Ile His Asp Asp Ser Leu Thr Phe
                805                 810                 815
Lys Glu Asp Ile Gln Lys Ala Gln Val Ser Gly Gln Gly Asp Ser Leu
                820                 825                 830
His Glu His Ile Ala Asn Leu Ala Gly Ser Pro Ala Ile Lys Lys Gly
            835                 840                 845
Ile Leu Gln Thr Val Lys Val Val Asp Glu Leu Val Lys Val Met Gly
850                 855                 860
Arg His Lys Pro Glu Asn Ile Val Ile Glu Met Ala Arg Glu Asn Gln
865                 870                 875                 880
Thr Thr Gln Lys Gly Gln Lys Asn Ser Arg Glu Arg Met Lys Arg Ile
                    885                 890                 895
Glu Glu Gly Ile Lys Glu Leu Gly Ser Gln Ile Leu Lys Glu His Pro
                900                 905                 910
Val Glu Asn Thr Gln Leu Gln Asn Glu Lys Leu Tyr Leu Tyr Tyr Leu
            915                 920                 925
Gln Asn Gly Arg Asp Met Tyr Val Asp Gln Glu Leu Asp Ile Asn Arg
            930                 935                 940
Leu Ser Asp Tyr Asp Val Asp His Ile Val Pro Gln Ser Phe Leu Lys
945                 950                 955                 960
Asp Asp Ser Ile Asp Asn Lys Val Leu Thr Arg Ser Asp Lys Asn Arg
                965                 970                 975
Gly Lys Ser Asp Asn Val Pro Ser Glu Glu Val Val Lys Lys Met Lys
                980                 985                 990
Asn Tyr Trp Arg Gln Leu Leu Asn Ala Lys Leu Ile Thr Gln Arg Lys
            995                 1000                1005
Phe Asp Asn Leu Thr Lys Ala Glu Arg Gly Gly Leu Ser Glu Leu
            1010                1015                1020
Asp Lys Ala Gly Phe Ile Lys Arg Gln Leu Val Glu Thr Arg Gln
            1025                1030                1035
Ile Thr Lys His Val Ala Gln Ile Leu Asp Ser Arg Met Asn Thr
            1040                1045                1050
Lys Tyr Asp Glu Asn Asp Lys Leu Ile Arg Glu Val Lys Val Ile
```

-continued

Thr Leu Lys Ser Lys Leu Val Ser Asp Phe Arg Lys Asp Phe Gln
1055                1060                1065
        1070                1075                1080

Phe Tyr Lys Val Arg Glu Ile Asn Asn Tyr His His Ala His Asp
        1085                1090                1095

Ala Tyr Leu Asn Ala Val Val Gly Thr Ala Leu Ile Lys Lys Tyr
        1100                1105                1110

Pro Lys Leu Glu Ser Glu Phe Val Tyr Gly Asp Tyr Lys Val Tyr
        1115                1120                1125

Asp Val Arg Lys Met Ile Ala Lys Ser Glu Gln Glu Ile Gly Lys
        1130                1135                1140

Ala Thr Ala Lys Tyr Phe Phe Tyr Ser Asn Ile Met Asn Phe Phe
        1145                1150                1155

Lys Thr Glu Ile Thr Leu Ala Asn Gly Glu Ile Arg Lys Arg Pro
        1160                1165                1170

Leu Ile Glu Thr Asn Gly Glu Thr Gly Glu Ile Val Trp Asp Lys
        1175                1180                1185

Gly Arg Asp Phe Ala Thr Val Arg Lys Val Leu Ser Met Pro Gln
        1190                1195                1200

Val Asn Ile Val Lys Lys Thr Glu Val Gln Thr Gly Gly Phe Ser
        1205                1210                1215

Lys Glu Ser Ile Leu Pro Lys Arg Asn Ser Asp Lys Leu Ile Ala
        1220                1225                1230

Arg Lys Lys Asp Trp Asp Pro Lys Lys Tyr Gly Gly Phe Asp Ser
        1235                1240                1245

Pro Thr Val Ala Tyr Ser Val Leu Val Val Ala Lys Val Glu Lys
        1250                1255                1260

Gly Lys Ser Lys Lys Leu Lys Ser Val Lys Glu Leu Leu Gly Ile
        1265                1270                1275

Thr Ile Met Glu Arg Ser Ser Phe Glu Lys Asn Pro Ile Asp Phe
        1280                1285                1290

Leu Glu Ala Lys Gly Tyr Lys Glu Val Lys Lys Asp Leu Ile Ile
        1295                1300                1305

Lys Leu Pro Lys Tyr Ser Leu Phe Glu Leu Glu Asn Gly Arg Lys
        1310                1315                1320

Arg Met Leu Ala Ser Ala Gly Glu Leu Gln Lys Gly Asn Glu Leu
        1325                1330                1335

Ala Leu Pro Ser Lys Tyr Val Asn Phe Leu Tyr Leu Ala Ser His
        1340                1345                1350

Tyr Glu Lys Leu Lys Gly Ser Pro Glu Asp Asn Glu Gln Lys Gln
        1355                1360                1365

Leu Phe Val Glu Gln His Lys His Tyr Leu Asp Glu Ile Ile Glu
        1370                1375                1380

Gln Ile Ser Glu Phe Ser Lys Arg Val Ile Leu Ala Asp Ala Asn
        1385                1390                1395

Leu Asp Lys Val Leu Ser Ala Tyr Asn Lys His Arg Asp Lys Pro
        1400                1405                1410

Ile Arg Glu Gln Ala Glu Asn Ile Ile His Leu Phe Thr Leu Thr
        1415                1420                1425

Asn Leu Gly Ala Pro Ala Ala Phe Lys Tyr Phe Asp Thr Thr Ile
        1430                1435                1440

Asp Arg Lys Arg Tyr Thr Ser Thr Lys Glu Val Leu Asp Ala Thr
        1445                1450                1455

```
Leu Ile His Gln Ser Ile Thr Gly Leu Tyr Glu Thr Arg Ile Asp
    1460            1465                1470
Leu Ser Gln Leu Gly Gly Asp Gly Gly Gly Ser Gly Thr Arg Leu
    1475            1480                1485
Pro Lys Lys Arg Lys Val Gly Gly Gly Ser Gly Ser Pro Ser
    1490            1495                1500
Lys Lys Asn Gly Arg Ser Gly Pro Gln Pro His Lys Arg Trp Val
    1505            1510                1515
Phe Thr Leu Asn Asn Pro Ser Glu Asp Glu Arg Lys Lys Ile Arg
    1520            1525                1530
Asp Leu Pro Ile Ser Leu Phe Asp Tyr Phe Ile Val Gly Glu Glu
    1535            1540                1545
Gly Asn Glu Glu Gly Arg Thr Pro His Leu Gln Gly Phe Ala Asn
    1550            1555                1560
Phe Val Lys Lys Gln Thr Phe Asn Lys Val Lys Trp Tyr Leu Gly
    1565            1570                1575
Ala Arg Cys His Ile Glu Lys Ala Lys Gly Thr Asp Gln Gln Asn
    1580            1585                1590
Lys Glu Tyr Cys Ser Lys Glu Gly Asn Leu Leu Met Glu Cys Gly
    1595            1600                1605
Ala Pro Arg Ser Gln Gly Gln Arg
    1610            1615
```

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
ctcccacctt tctcatccaa g                                    21

<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 18
acatcacccc tctacctcc                                       19

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
gagactggct cttaaaaagt gc                                   22

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20

```
gctaatcttc ttgaacagcc g                                              21

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 21
ctgacaactc ttttcatctt ct                                             22

<210> SEQ ID NO 22
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 22
aaagtgcagg gtctggcg                                                  18

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
atgagcttgc tcctcccaaa cc                                             22

<210> SEQ ID NO 24
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 24
tcactactta ccttgctgga cc                                             22
```

MATERIALS AND METHODS FOR INCREASING GENE EDITING FREQUENCY

CROSS-REFERENCE TO RELATED APPLICATIONS

This application is a National Stage application under 35 U.S.C. § 371 of International Application No. PCT/US2018/037353, having an International Filing Date of Jun. 13, 2018, which claims benefit of priority from U.S. Provisional Application Ser. No. 62/518,960, filed on Jun. 13, 2017. The disclosures of the prior applications are considered part of (and are incorporated by reference in) the disclosure of this application.

STATEMENT AS TO FEDERALLY SPONSORED RESEARCH

This invention was made with government support under GM119483 awarded by the National Institutes of Health. The government has certain rights in the invention.

SEQUENCE LISTING

This document includes a sequence listing submitted to the United States Patent and Trademark Office via the electronic filing system as an ASCII text file. The sequence listing, which is incorporated-by-reference herein, is titled "SEQ.TXT," was created on Dec. 13, 2019, and has a size of 60.5 kilobytes.

TECHNICAL FIELD

This document relates to improved materials and methods for gene editing using endonucleases and endonuclease systems, such as the Clustered Regularly Interspaced Short Palindromic Repeats (CRISPR)/CRISPR-associated protein 9 (Cas9) endonuclease system. For example, the methods provided herein include the use of a tag to couple a donor nucleic acid sequence to a CRISPR/Cas9 complex, thus increasing the efficiency with which the donor nucleic acid is transferred into a targeted sequence.

BACKGROUND

Gene editing can be used to generate various types of targeted mutations within the genome of cells, including mutations to correct point mutations, mutations to knock-out or knock-in aberrant protein function, and mutations to introduce coding or noncoding regions of the genome where they are lacking. The CRISPR/Cas9 system provides a versatile and powerful tool for editing the genome at virtually any point by first introducing a double strand break or single strand nick at a specific site (via the Cas9 enzyme and a specially designed guide RNA), and then allowing DNA repair mechanisms to (1) rejoin the two ends in a process called Non-homologous End Joining (NHEJ), which can disrupt the gene by introducing a stop codon or a frameshift mutation, or (2) insert a region of DNA (donor DNA) containing modifications of interest (e.g., point mutations, insertions of sequences such as epitope tags, or deletions) via a process called Homology Directed Repair (HDR). A donor DNA can be, for example, a single strand oligonucleotide, a plasmid, or linearized DNA; the donor DNA can be transfected or electroporated into cells along with one or more plasmids containing the Cas9 and the guide RNA (gRNA) or with a preassembled recombinant Cas9 protein/gRNA complex (Livak and Schmittgen *Methods* 25(4):402-408, 2001). The HDR editing process tends to be inefficient compared to the formation of DNA nicks/breaks, however, perhaps because the competing pathway of NHEJ is more efficient than the delivery and integration of donor DNA.

SUMMARY

This document is based, at least in part, on the discovery that a Cas9 enzyme can be fused to an HUH tag, thereby allowing covalent tethering of a donor DNA molecule to a Cas9-HUH/gRNA complex, and providing a means for delivery, to a target nucleotide sequence, of a single complex containing all the components required for DNA cleavage and HDR. The enhanced bio-availability of donor DNA at sites of Cas9 activity may enhance the efficiency of gene editing, overcoming a substantial hurdle in using gene-editing for disease therapy.

Thus, in a first aspect, this document features a method for modifying the genetic material of a cell, where the method includes introducing into the cell a ribonucleic acid protein (RNP) complex, where the RNP complex contains (a) a polypeptide including a Cas9 endonuclease and an HUH tag, (b) a guide RNA targeted to a selected sequence in the genome of the cell, and (c) a donor DNA containing a single-stranded target sequence that can specifically interact with the HUH tag, wherein, after the introducing, the guide RNA directs the RNP complex to the selected sequence, the Cas9 endonuclease induces a nick or a double strand break at or near the selected sequence, and the donor DNA is inserted at the double stranded break. The polypeptide can include a linker between the Cas9 endonuclease and the HUH tag. The HUH tag can be at the N-terminus of the Cas9 endonuclease polypeptide, or at the C-terminus of the Cas9 endonuclease polypeptide. The Cas9 endonuclease can contain one or more mutations as compared to the Cas9 endonuclease having the amino acid sequence set forth in SEQ ID NO:14 or SEQ ID NO:15. The one or more mutations can reduce the endonuclease activity of the Cas9, reduce non-specific activity of the Cas9, or cause the Cas9 polypeptide to have nickase activity rather than double strand cleavage activity. The method can include introducing the RNP complex into the cell using a cationic lipid, electroporation, or injection. The RNP complex can be attached to an antibody, a nanobody, or an ScFv that binds to a cell-surface antigen of the cell, or can be attached to a gold nanoparticle or a cell-penetrating polypeptide.

In another aspect, this document features a fusion polypeptide comprising a Cas9 polypeptide and an HUH tag. The polypeptide can further include a linker (e.g., a linker positioned between the Cas9 polypeptide and the HUH tag). The HUH tag can be fused to the N-terminus of Cas9, or to the C-terminus of Cas9. The Cas9 polypeptide can include mutations that disable its catalytic activity, reduce non-specific cutting, or cause it to nick instead of induce a double strand break.

In another aspect, this document features a RNP molecular complex. In general, this complex can include a recombinant Cas9/HUH tag fusion polypeptide, a gRNA that recognizes a specific site in the genome of a cell, and a piece of DNA containing a single-stranded target sequence recognized by the HUH tag. The DNA can be, for example, an oligonucleotide [e.g., a single-stranded oligodeoxynucleotide (ssODN)] or a PCR product with a single-strand overhang generated by incorporating a spacer nucleotide into the PCR product, which a polymerase cannot read through. In some embodiments, a ssODN can be annealed to a complementary oligonucleotide that is covalently attached to the HUH tag. The DNA can include one or more "homology arms," sequences with homology to a genomic sequence near the sequence recognized by the gRNA. The DNA can include a linker between the HUH tag target sequence and the homology arms (e.g., on the ssODN) or other DNA, and the linker can be varied.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A: SDS-PAGE showing Nickel affinity purification of the Cas9 and Cas9-PCV proteins. The lanes labeled Cas9 and Cas9-PCV on the right side of the gels show the elution fractions of the protein from the Nickel columns. FIG. 1B: SDS-PAGE gel showing cation exchange purification after nickel affinity purification. The Cas9 and Cas9-PCV proteins are the dominant species, demonstrating that the two-step purification produced high-quality protein.

FIG. 4 shows that covalent tethering resulted in a 2- to 3-fold increase in incorporation of the luciferase tag (HiBIT; Promega). This effect was only observed when the PCV target was present on the ssODN.

As shown in FIG. 5A, enhancements up to 3-fold were observed when 1.5 or 3 pmol Cas9-PCV was used. Enhancements up to about 30-fold were observed when lower concentrations of RNP were used (FIG. 5B).

FIGS. 6A, 6B, and 6C show that covalent tethering of the donor DNA enhanced HDR when assayed at the DNA level. Quantitative polymerase chain reaction (qPCR; also referred to as real-time PCR) was performed on cell lysates from FIG. 5 with two sets of primers—a GAPDH set that annealed to unmodified GAPDH, and a HiBIT set that annealed to luciferase-tag modified GAPDH. FIG. 6A is a graph showing that the amplification efficiencies of the primers were equivalent, meaning that cycle threshold values could be compared. The cycle threshold times are shown in FIG. 6B for triplicate measurements for both sets of primers for PCV or PCV-Cas9. The cycle threshold values were used to calculate the relative incorporation of HiBIT into GAPDH. A two-fold enhancement of HDR efficiency was calculated (FIG. 6C), demonstrating that covalent tethering of the donor DNA to Cas9-PCV enhanced HDR.

DETAILED DESCRIPTION

Figure 1:
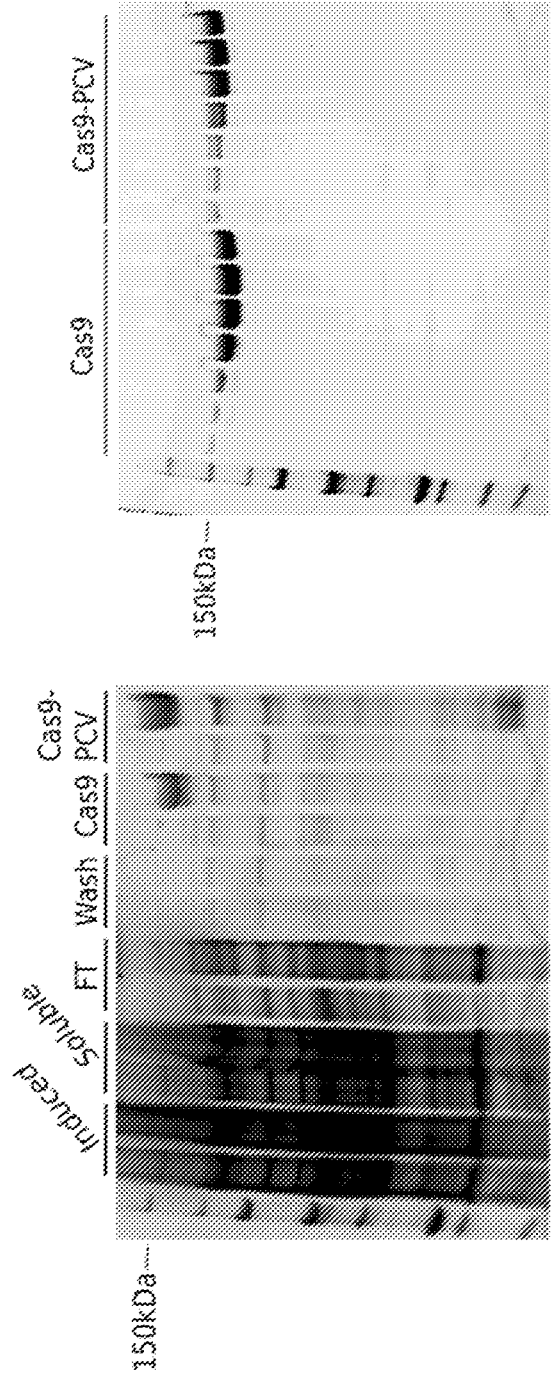
FIGS. 1A and 1B are images of sodium dodecyl sulfate polyacrylamide gel electrophoresis (SDS-PAGE) gels demonstrating expression and purification of PCV2-Cas9 fusions from *E. coli*.

As described herein, a tag that can form covalent links with single-stranded DNA, referred to herein as an HUH tag, can be fused to a targeted endonuclease (e.g., a Cas9 endonuclease) in order to allow for covalent tethering (via the HUH tag) of a donor DNA to the endonuclease or, in the case of Cas9, to the Cas9/gRNA complex, thus permitting delivery into cells of a single complex containing all components required for DNA cleavage and HDR. Enhanced availability of donor DNA at sites of endonuclease activity can greatly enhance the efficiency of gene editing, overcoming a substantial hurdle in using gene editing for disease therapy. Other potential applications of HUH tagged endonuclease fusions also are contemplated, including the use of such fusions to specifically tag the genome with bright fluorophores incorporated into DNA oligonucleotides that are covalently linked to the HUH tag coupled to a catalytically-dead endonuclease (e.g., a catalytically dead Cas9 combined with a gRNA such as a single-guide RNA (sgRNA) for directing the Cas9 to a specific sequence).

Thus, this document provides fusion polypeptides containing an endonuclease (e.g., a Cas9 endonuclease) and an HUH tag. In addition, this document provides nucleic acids encoding the fusion polypeptides, and methods for using the polypeptides and/or nucleic acids to achieve modify the genomic DNA within a cell.

The term "polypeptide" as used herein refers to a compound of two or more subunit amino acids, regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from cellular components with which it normally is found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

The terms "nucleic acid" and "polynucleotide" can be used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The nucleic acids may be incorporated into or contained within recombinant nucleic acid constructs such as vectors. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more "expression control sequences" that control or regulate the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available.

Host cells containing a nucleic acid or vector also are provided herein. Suitable host cells can include, without limitation, bacterial cells, yeast cells, and human or non-human mammalian cells (e.g., HEK 293 cells, 3T3 cells, or HeLa cells).

The fusion polypeptides described herein can include a Cas9 polypeptide sequence and any suitable HUH sequence, which can be derived from any appropriate source. Representative HUH sequences include, without limitation, the amino acid sequences set forth in SEQ ID NOS:1-13. Additional information regarding HUH-containing proteins is found elsewhere (see, e.g., U.S. Publication No. 2016/0340395, which is incorporated herein by reference in its entirety).

```
(porcine circovirus 2 (PCV2)):
                                      SEQ ID NO: 1
SPSKKNGRSGPQPHKRWVFTLNNPSEDERKKIRDLPISLFDYFIVGEEGNE

EGRTPHLQGFANFVKKQTFNKVKWYLGARCHIEKAKGTDQQNKEYCSKEGN

LLMECGAPRSQGQR (GeneA from PhiX174 Y131H mutant):
                                      SEQ ID NO: 2
KSRRGFAIQRLMNAMRQAHADGWFIVFDTLTLADDRLEAFYDNPNALRDYF

RDIGRMVLAAEGRKANDSHADCYQYFCVPEYGTANGRLHFHAVHFMRTLPT

GSVDPNFGRRVRNRRQLNSLQNTWPYGHSMPIAVRYTQDAFSRSGWLWPVD

AKGEPLKATSYMAVGFYVAKYVNKKSDMDLAAKGLGAKEWNNSLKTKLSLL

PKKLFRIRMSRNFGMKMLTMTNLSTECLIQLTKLGYDATPFNQILKQNAKR

EMRLRLGKVTVADVLAAQPVTTNLLKFMRASIKMIGVSNLQSFIASMTQKL

TLSDISDESKNYLDKAGITTACLRIKSKWTAGGK
```

-continued (mMob mobilization protein from *Escherichia coli*):
SEQ ID NO: 3
MAIYHLTAKTGSRSGGQSARAKAD_YIQREGKYARDMDEVLHAESGHMPEFV

ERPADYWDAADLYERANGRLFKEVEFALPVELTLDQQKALASEFAQHLTGA

ERLPYTLAIHAGGGENP_HC_HLMISERINDGIERPAAQWFKRYNGKTPEKGG

AQKTEALKPKAWLEQTREAWADHANRALERAGH (TraI DNA-nicking and unwinding protein):
SEQ ID NO: 4
MMSIAQVRSAGSAGN_YY_TDKDNYYVLGSMGERWAGRGAEQLGLQGSVDKDV

FTRLLEGRLPDGADLSRMQDGSNRHRPGYDLTFSAPKSVSMMAMLGGDKRL

IDAHNQAVDFAVRQVEALASTRVMTDGQSETVLTGNLVMALFNHDTSRDQE

PQL_HT_HAVVANVTQHNGEWKTLSSDKVGKTGFIENVYANQIAFGRLYREKL

KEQVEALGYETEVVGKHGMWEMPGVPVEAFSGRSQTIREAVGEDASLKSRD

VAALDTRKSKQHVDPEIKMAEWMQTLKETGFDIRAYRDAADQRADLRTLTP

GPASQDGPDVQQAVTQAIAGLSER (RepB replication protein from *Streptococcus agalactiae*):
SEQ ID NO: 5
MAKEKARYFTFLLYPESIPSDWELKLETLGVPMAISPLHDKDKSSIKGQKY

KKA_HY_HVLYIAKNPVTADSVRKKIKLLLGEKSLAMVQVVLNVENMYL_YL_TH

ESKDAIAKKKHVYDKADIKLINNFDIDRYLE (RepB replication protein from *Streptococcus pneumonia*):
SEQ ID NO: 6
MSEKKEIVKGRDWTFLVYPESAPENWRTILDETFMRWVESPLHDKDVNADG

EIKKPHWHILLSSDGPITQTAVQKIIGPLNCPNAQKVGSAKGLVRYMVHLD

NPEKYQYSLDEIVGHNGADVASYFELTA (master replication protein from Fava bean necrotic yellow virus (FBNYV)):
SEQ ID NO: 7
MARQVICWCFTLNNPLSPLSLHDSMKYLVYQTEQGEAGNI_H_FQGYIEMKKR

TSLAGMKKLIPGAHFEKRRGTQGEARA_Y_SMKEDTRLEGPWEYGEFVP (NES nicking protein from *Staphylococcus aureus*):
SEQ ID NO: 8
AMYHFQNKFVSKANGQSATAKSA_YN_SASRIKDFKENEFKDYSNKQCDYSEI

LLPNNADDKFKDREYLWNKVHDVENRKNSQVAREIIIGLPNEFDPNSNIEL

AKEFAESLSNEGMIVDLNIHKINEENP_HA_HLLCTLRGLDKNNEFEPKRKGN

DYIRDWNTKEKHNEWRKRWENVQNKHLEKNGFSVRVSADSYKNQNIDLEPT

KKEGWKARKFEDETG (TrwC conjugative relaxase):
SEQ ID NO: 9
MLSHMVLTRQDIGRAASYYEDGADDYYAKDGDASEWQGKGAEELGLSGEVD

SKRFRELLAGNIGEGHRIMRSATRQDSKERIGLDLTFSAPKSVSLQALVAG

DAEIIKAHDRAVARTLEQAEARAQARQKIQGKTRIETTGNLVIGKFRHETS

RERDPQL_H_THAVILNMTKRSDGQWRALKNDEIVKATRYLGAVYNAELAHEL

QKLGYQLRYGKDGNFDLAHIDRQQIEGFSKRTEQIAEWYAARGLDPNSVSL

EQKQAAKVLSRAKKTSVDREALRAEWQATAKELGIDFS (VirD2-T-DNA border endonuclease):
SEQ ID NO: 10
MPDRAQVIIRIVPGGGTKTLQQIINQLEYLSRKGRLELQRSARHLDIPLPP

DQIHELARSWVQETGTYDESQPDEERQQELTTHIIVSFPAGTSQVAAYAAS

REWAAEMFGSGAGGGRYNYLTAFHIDRDHPHLHVVVNRRELLGHGWLKISR

RHPQLNYDALRIKMAEISLRHGIALDASRRAERGITERPITYAQYRRLERE

QARQIRFEDADLEQSSPQGDHPEFSQPFDTSPFEASAGGPEDMPRPNNRQN

ES (replication associated protein for *Tomato yellow leaf curl virus* (TLYCV)):
SEQ ID NO: 11
MPRLFKIYAKNYFLTYPNCSLSKEEALSQLKKLETPTNKKYIKVCKELHEN

GEP_HL_HVLIQFEGKYQCKNQRFFDLVSPNRSAHFHPNIQAAKSSTDVKT_YV_

EKDGNFIDFGVSQIDGRS (RepBm-Plasmid replication protein RepB from *Streptococcus pneumoniae*):
SEQ ID NO: 12
MSEKKEIVKGRDWTFLVYPESAPENWRTILDETFMRWVESPLHDKDVNADG

EIKKPHWHILLSSDGPITQTAVQKIIGPLNCPNAQKVGSAKGLVRYMVHLD

NPEKYQYSLDEIVGHNGADVASYFELTA (DCV-duck circovirus):
SEQ ID NO: 13
MAKSGNYSYKRWVFTINNPTFEDYVHVLEFCTLDNCKFAIVGEEKGANGTP

HLQGFLNLRSNARAAALEESLGGRAWLSRARGSDEDNEE_Y_CAKESTYLRVG

EPVSKGRSS

HUH proteins are endonucleases that can recognize and form stable covalent bonds with specific sequences of unmodified DNA, and the native covalent DNA linking ability of HUH proteins allows for their use to couple DNA to a Cas9 protein, as described herein. Thus, the HUH tags that can be included in the fusion polypeptides described herein can include an HUH endonuclease domain. HUH endonuclease domains are present in many viral replication proteins, relaxases, and transposases.

HUH endonucleases have a small "nicking domain" that, in isolation, can bind and nick specific single-stranded DNA sequences, subsequently forming a covalent link (e.g., a phosphotyrosine ester) between the protein and the 5' end of the DNA strand. The nicking activity of HUH endonucleases typically involves coordinating a metal ion (e.g., a magnesium ion, a nickel ion, or a manganese ion) in the active site by two conserved histidines and a polar residue ("U") that form the catalytic "HUH motif," although it is noted that the HUH motif may contain only one histidine residue. Exemplary metal-coordinating histidine residues are indicated by underlining at residue 57 of SEQ ID NO:1, residues 90 and 92 of SEQ ID NO:2, residues 120 and 122 of SEQ ID NO:3, residues 157 and 159 of SEQ ID NO:4, residues 55 and 57 of SEQ ID NO:5, residue 41 of SEQ ID NO:7, residues 130 and 132 of SEQ ID NO:8, residues 161 and 163 of SEQ ID NO:9, residues 55 and 57 of SEQ ID NO:11, residues 57 and 59 of SEQ ID NO:12, and residue 52 of SEQ ID NO:13. The catalytic polar residue of an HUH protein often is a tyrosine residue, but it is noted that any suitable catalytic polar amino acid residue (e.g., serine, threonine, or cysteine) can be used. Exemplary polar catalytic amino acid residues are indicated by italics and underlining at residue 96 of SEQ ID NO:1, residue 128 of SEQ ID NO:2, residue 25 of SEQ ID NO:3, residue 16 of SEQ ID NO:4, residue 99 of SEQ ID NO:5, residue 79 of SEQ ID NO:7, residue 24 of SEQ ID NO:8, residue 26 of SEQ ID NO:9, residue 101 of SEQ ID NO:11, residue 97 of SEQ ID NO:12, and residue 91 of SEQ ID NO:13.

In some cases, the fusion polypeptides provided herein can include a functional fragment of an HUH polypeptide, where the functional fragment includes the metal-coordinating residue or residues (typically histidine) and the polar amino acid residue of the catalytic motif, as well as sufficient additional amino acids to allow the HUH fragment to possess DNA nicking activity. Exemplary HUH fragments that can be used as tags in the fusion polypeptides provided herein include, without limitation, amino acids 16-99 (with or without a deletion within amino acids 46-55) of SEQ ID NO:1, amino acids 6-126 of SEQ ID NO:3, amino acids 6-101 of SEQ ID NO:5, amino acids 7-94 of SEQ ID NO:7, amino acids 12-98 of SEQ ID NO:12, and amino acids 11-101 of SEQ ID NO:13.

In some cases, an HUH tag can include one or more amino acid sequence modifications with respect to the amino acid sequences provided herein. For example, an HUH tag sequence can include a deletion of one or more amino acid residues (e.g., one or more of amino acids 46-55 of SEQ ID NO:1), or can include an amino acid substitution (e.g., a conservative amino acid substitution). Conservative substitutions for a particular amino acid residue in a reference sequence typically can be selected from other members of the class to which the amino acid residue belongs. For example, an amino acid belonging to a group of amino acids having a particular size or characteristic (such as charge, hydrophobicity, or hydrophilicity) can be substituted for another amino acid within the group, without altering the activity and/or structure of the polypeptide. Examples of amino acid groupings include nonpolar (hydrophobic) amino acids (alanine, leucine, isoleucine, valine, proline, phenylalanine, tryptophan, and tyrosine), polar neutral amino acids (glycine, serine, threonine, cysteine, tyrosine, asparagine, and glutamine), positively charged (basic) amino acids (arginine, lysine, and histidine), and negatively charged (acidic) amino acids (aspartic acid and glutamic acid). Thus, exemplary conservative substitutions include, without limitation, Lys for Arg or Arg for Lys to maintain a positive charge, Glu for Asp or Asp for Glu to maintain a negative charge, Ser for Thr so that a free —OH is maintained, and Gln for Asn to maintain a free —NH$_2$.

In some cases, a fusion polypeptide as provided herein (e.g., a fusion polypeptide containing a Cas9 endonuclease and an HUH tag) can include an HUH tag having the amino acid sequence set forth in any one of SEQ ID NOS:1 to 13. In some cases, a fusion polypeptide can include a functional fragment of any of SEQ ID NOS:1 to 13, where the functional fragment includes an HUH catalytic motif and has the ability to bind to a DNA sequence. In some cases, a fusion polypeptide can include a HUH tag with an amino acid sequence that includes one or more variations (e.g., amino acid deletions, additions, or substitutions) as compared to SEQ ID NOS:1 to 13. Such an HUH tag can have an amino acid sequence that is at least 90% (e.g., at least 92%, at least 95%, at least 97%, at least 98%, at least 99%, 90 to 93%, 93 to 95%, 95 to 98%, or 98 to 99.9%) identical to a sequence as set forth in any of SEQ ID NOS:1 to 13.

A fusion polypeptide described herein (e.g., a fusion polypeptide containing a Cas9 endonuclease and an HUH tag) can include any appropriate Cas9 endonuclease. The Cas9 protein includes two distinct active sites—a RuvC-like nuclease domain and a HNH-like nuclease domain, which generate site-specific nicks on opposite DNA strands (Gasiunus et al., *Proc Natl Acad Sci USA* 109(39):E2579-E2586, 2012). The RuvC-like domain is near the amino terminus of the Cas9 protein and is thought to cleave the target DNA that is noncomplementary to the crRNA, while the HNH-like domain is in the middle of the protein and is thought to cleave the target DNA that is complementary to the crRNA. A representative Cas9 sequence from *Streptococcus thermophilus* is set forth in SEQ ID NO:14 (see, also, UniProtKB number Q03JI6), and a representative Cas9 sequence from *S. pyogenes* is set forth in SEQ ID NO:15 (see, also, UniProtKB number Q99ZW2).

(*S. thermophilus*):

SEQ ID NO: 14

MTKPYSIGLDIGTNSVGWAVTTDNYKVPSKKMKVLGNTSKKYIKKNLLGVL

LFDSGITAEGRRLKRTARRRYTRRRNRILYLQEIFSTEMATLDDAFFQRLD

DSFLVPDDKRDSKYPIFGNLVEEKAYHDEFPTIYHLRKYLADSTKKADLRL

VYLALAHMIKYRGHFLIEGEFNSKNNDIQKNFQDFLDTYNAIFESDLSLEN

SKQLEEIVKDKISKLEKKDRILKLFPGEKNSGIFSEFLKLIVGNQADFRKC

FNLDEKASLHFSKESYDEDLETLLGYIGDDYSDVFLKAKKLYDAILLSGFL

TVTDNETEAPLSSAMIKRYNEHKEDLALLKEYIRNISLKTYNEVFKDDTKN

GYAGYIDGKTNQEDFYVYLKKLLAEFEGADYFLEKIDREDFLRKQRTFDNG

SIPYQIHLQEMRAILDKQAKFYPFLAKNKERIEKILTFRIPYYVGPLARGN

SDFAWSIRKRNEKITPWNFEDVIDKESSAEAFINRMTSFDLYLPEEKVLPK

HSLLYETFNVYNELTKVRFIAESMRDYQFLDSKQKKDIVRLYFKDKRKVTD

KDIIEYLHAIYGYDGIELKGIEKQFNSSLSTYHDLLNIINDKEFLDDSSNE

AIIEEIIHTLTIFEDREMIKQRLSKFENIFDKSVLKKLSRRHYTGWGKLSA

KLINGIRDEKSGNTILDYLIDDGISNRNFMQLIHDDALSFKKKIQKAQIIG

DEDKGNIKEVVKSLPGSPAIKKGILQSIKIVDELVKVMGGRKPESIVVEMA

RENQYTNQGKSNSQQRLKRLEKSLKELGSKILKENIPAKLSKIDNNALQND

RLYLYYLQNGKDMYTGDDLDIDRLSNYDIDHIIPQAFLKDNSIDNKVLVSS

ASNRGKSDDVPSLEVVKKRKTFWYQLLKSKLISQRKFDNLTKAERGGLSPE

DKAGFIQRQLVETRQITKHVARLLDEKFNNKKDENNRAVRTVKIITLKSTL

VSQFRKDFELYKVREINDFHHAHDAYLNAVVASALLKKYPKLEPEFVYGDY

PKYNSFRERKSATEKVYFYSNIMNIFKKSISLADGRVIERPLIEVNEETGE

SVWNKESDLATVRRVLSYPQVNVVKKVEEQNHGLDRGKPKGLFNANLSSKP

KPNSNENLVGAKEYLDPKKYGGYAGISNSFTVLVKGTIEKGAKKKITNVLE

FQGISILDRINYRKDKLNFLLEKGYKDIELIIELPKYSLFELSDGSRRMLA

SILSTNNKRGEIHKGNQIFLSQKFVKLLYHAKRISNTINENHRKYVENHKK

EFEELFYYILEFNENYVGAKKNGKLLNSAFQSWQNHSIDELCSSFIGPTGS

ERKGLFELTSRGSAADFEFLGVKIPRYRDYTPSSLLKDATLIHQSVTGLYE

TRIDLAKLGEG (*S. pyogenes*):

SEQ ID NO: 15

MDKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

-continued

```
IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYEKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD
```

Thus, the materials and methods provided herein can utilize a Cas9 polypeptide having the sequence of SEQ ID NO:14 or SEQ ID NO:15. In some embodiments, however, the methods described herein can be carried out using a Cas9 functional variant having at least 80% (e.g., at least 85%, at least 90%, at least 95%, or at least 98%) sequence identity with SEQ ID NO:14 or SEQ ID NO:15. Thus, in some embodiments, a polypeptide (e.g., a fusion polypeptide containing Cas9 and an HUH tag) can contain one or more amino acid substitutions, deletions, or additions as compared to the sequence set forth in SEQ ID NO:14. In certain cases, polypeptides containing such changes can have at least 80% (e.g., at least 85%, 90%, 91%, 92%, 93%, 94%, 95%, 96%, 97%, 98%, or 99%) sequence identity to SEQ ID NO:15. The activity of a functional Cas9 variant may be altered as compared to the corresponding unmodified Cas9 polypeptide. For example, by modifying specific amino acids in the Cas9 protein that are responsible for DNA cleavage, the Cas9 can function as a DNA nickase (Jinek et al., *Science* 337:816-821, 2012), or as a DNA binding protein that has no nuclease or nickase activity but is capable of interacting with DNA to interfere with incoming proteins (Qi et al. *Cell* 152:1173-1183, 2013).

In some embodiments, therefore, a Cas9 protein may not have double-stranded nuclease activity, but may have nickase activity such that it can generate one or more single strand nicks within a preselected target sequence when complexed with a gRNA. For example, a Cas9 polypeptide can have a D10A substitution in which an alanine residue is substituted for the aspartic acid at position 10, resulting in a nickase. In some cases, a Cas9 polypeptide can have an H840A substitution in which an alanine residue is substituted for the histidine at position 840, resulting in a "nuclease-dead" Cas9 that has neither nuclease nor nickase activity, but can bind to a preselected target sequence when complexed with a gRNA. A Cas9 polypeptide also can include a combination of D10A and H840A substitutions, or D10A, D839A, H840A, and N863A substitutions. See, e.g., Mali et al., *Nature Biotechnol*, 31:833-838, 2013.

Amino acid substitutions also can be made by selecting conservative substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of conservative substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. In some embodiments, an amino acid substitution can be non-conservative, such that a member of one of the amino acid classes described above is exchanged for a member of another class.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output-.txt -q -1 -r2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:15), or by an articulated length (e.g., 100 consecutive nucleotides or amino acid residues from a sequence set forth in an identified sequence), followed by multiplying the resulting value by 100. For example, an amino acid sequence that has 1300 matches when aligned with the sequence set forth in SEQ ID NO:15 is 95 percent identical to the sequence set forth in SEQ ID NO:15 (i.e., 1300÷1368×100=95). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

In some cases, a fusion polypeptide described herein (e.g., a fusion polypeptide containing a Cas9 endonuclease and an HUH tag) can include a second tag (e.g., a protein tag). Examples of protein tags include, without limitation, small ubiquitin-like modifier (SUMO) polypeptides. In cases, where a fusion polypeptide containing a Cas9 endonuclease and an HUH tag also includes a SUMO tag, the fusion polypeptide can include the sequence set forth below.

(SUMO-Cas9-NLS-PCV)
SEQ ID NO: 16
MRGSHHHHHHMASGSDSEVNQEAKPEVKPEVKPETHINLKVSDGSSEIFFK

IKKTTPLRRLMEAFAKRQGKEMDSLRFLYDGIRTQADQTPEDLDMEDNDII

EAHREQIGGSMDKKYSIGLDIGTNSVGWAVITDEYKVPSKKFKVLGNTDRH

SIKKNLIGALLFDSGETAEATRLKRTARRRYTRRKNRICYLQEIFSNEMAK

VDDSFFHRLEESFLVEEDKKHERHPIFGNIVDEVAYHEKYPTIYHLRKKLV

DSTDKADLRLIYLALAHMIKFRGHFLIEGDLNPDNSDVDKLFIQLVQTYNQ

LFEENPINASGVDAKAILSARLSKSRRLENLIAQLPGEKKNGLFGNLIALS

LGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDL

LRKQRTFDNGSIPHQIHLGELHAILRRQEDFYPFLKDNREKIEKILTFRIP

YYVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKIIK

DKDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLTF

KEDIQKAQVSGQGDSLHEHIANLAGSPAIKKGILQTVKVVDELVKVMGRHK

PENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVL

TRSDKNRGKSDNVPSEEVVKKMKNYWRQLLNAKLITQRKFDNLTKAERGGL

SELDKAGFIKRQLVETRQITKHVAQILDSRMNTKYDENDKLIREVKVITLK

SKLVSDFRKDFQFYKVREINNYHHAHDAYLNAVVGTALIKKYPKLESEFVY

GDYKVYDVRKMIAKSEQEIGKATAKYFFYSNIMNFFKTEITLANGEIRKRP

LIETNGETGEIVWDKGRDFATVRKVLSMPQVNIVKKTEVQTGGFSKESILP

KRNSDKLIARKKDWDPKKYGGFDSPTVAYSVLVVAKVEKGKSKKLKSVKEL

LGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHY

LDEIIEQISEFSKRVILADANLDKVLSAYNKHRDKPIREQAENIIHLFTLT

NLGAPAAFKYFDTTIDRKRYTSTKEVLDATLIHQSITGLYETRIDLSQLGG

DGGGSGTRLPKKKRKVGGGSGSPSKKNGRSGPQPHKRWVFTLNNPSEDERK

KIRDLPISLFDYFIVGEEGNEEGRTPHLQGFANFVKKQTFNKVKWYLGARC

HIEKAKGTDQQNKEYCSKEGNLLMECGAPRSQGQR

The donor DNA used with the HUH-tagged endonuclease in the methods provided herein can be single stranded or can be double stranded but have a single stranded overhang at one or both ends, and can have homology to a particular sequence within the genome of the cells or organism of interest. Typically, a donor DNA includes a nucleic acid sequence that will replace an endogenous target sequence within the cells of interest, flanked by sequences homologous to endogenous sequences on either side of the target. The donor DNA can have a length of about 25 nt to about 500 nt (e.g., 25 to 50 nt, 50 to 100 nt, 100 to 200 nt, 200 to 300 nt, 300 to 400 nt, or 400 to 500 nt). Within the donor DNA, the flanking homologous sequences (also referred to as "homology arms") can have any suitable length (e.g., 5 to 10 nt, 10 to 15 nt, 15 to 20 nt, 20 to 25 nt, 25 to 50 nt, 50 to 75 nt, or 75 to 100 nt). Donor DNA molecules can be obtained commercially or using any suitable technique.

It is noted that endonucleases other than CRISPR/Cas9 systems can be used in the methods provided herein. For example, other endonucleases that can target a particular nucleotide sequence and generate a nick or a double strand break at or near that sequence can be used. Examples of such endonucleases, which are rare-cutting and can be customizable, include zinc finger nucleases (ZFNs), meganucleases (MNs), and transcription activator-like effector (TALE) endonucleases. See, for example, Zhang et al., *Proc Natl Acad Sci USA*, 107(26):12028-12033, 2010; Sander et al., *Nature Methods*, 8:67-69, 2011; Jacoby et al., *Nucl Acids Res*, 10.1093/nar/gkr1303, 2012); Christian et al., *Genetics*, 186:757-761, 2010; U.S. Publication No. 2011/0145940, for discussions of these endonucleases.

This document also provides methods for modifying the genetic material of a cell (e.g., a plant cell, an animal cell, or a bacterial, yeast, or fungal cell). The methods can include introducing into a cell, or a population of cells, a RNP complex that includes (a) a fusion polypeptide containing an HUH tag and an endonuclease or a portion thereof, where the endonuclease is targeted to a selected sequence in the genome of the cell, and (b) a donor DNA that includes a single-stranded target sequence that can specifically interact with the HUH tag. In some cases, the endonuclease can be a Cas9 polypeptide with nuclease or nickase activity, and the RNP also can include a guide RNA that targets the Cas9 polypeptide to a selected target sequence in the genome of the cell. After the RNP complex is introduced into the cells, the RNP complex can interact with the selected sequence (e.g., directed by the guide RNA when the endonuclease is Cas9), the endonuclease can induce a nick or a double strand break at or near the selected sequence, and the donor DNA can be inserted at the nick or double stranded break.

Any suitable method can be used to introduce an RNP complex into a cell. For example, an RNP complex can be delivered by cationic lipid, electroporation, injection, attachment to an antibody, nanobody, or ScFv targeting a cell-surface antigen, attachment to a gold nanoparticle, or attachment to a cell penetrating peptide (also referred to as a protein transduction domains, membrane translocating sequence, or Trojan peptide), a highly cationic, short peptide about 40 amino acids or less in length, that typically is rich in arginine and lysine and has the ability to gain access to the interior of almost any cell.

The invention will be further described in the following example, which does not limit the scope of the invention described in the claims.

EXAMPLE

Methods

Cas9 protein expression: Cas9 was purchased from Integrated DNA Technologies. PCV-Cas9 was constructed by inserting the Cas9 coding sequence between the SUMO and PCV2 proteins at the BamHI site in pTD68_SUMO-PCV2 using Infusion cloning. Cas9-PCV2 were purified according to methods described elsewhere (see, e.g., Anders and Jinek, 2015 *Methods Enzymol* 558:515). Proteins were expressed in *E. coli* BL21(DE3) that were grown in autoinduction media for ~8 hours at 37° C. and then shifted to 25° C. for 24 hours. Cells were collected by centrifugation, resuspended in lysis buffer [20 mM Tris-HCl, pH 8.0, 500 mM NaCl, 5 mM imidazole, 0.4 mM 4-(2-aminoethyl)benzenesulfonyl fluoride hydrochloride (AEBSF)], and lysed by sonication. Soluble protein was bound to Ni-NTA agarose (ThermoFisher), washed with ~15 column volumes lysis buffer, and eluted in 20 mM Tris, pH 8.0, 500 mM NaCl, 500 mM imidazole. The eluate was dialyzed overnight at 4° C. against 20 mM 4-(2-hydroxyethyl)-1-piperazineethanesulfonic acid (HEPES), pH 7.5, 150 mM KCl, 1 mM ethylenediaminetetraacetic acid (EDTA), 1 mM dithiothreitol (DTT), 10% glycerol. The SUMO tag of Cas9-PCV2 was removed with recombinant Ulp1 protease during dialysis. Dialyzed protein was bound to a HiTrap SP HP column (1 mL, GE Healthcare; Wilmington, Mass.) equilibrated in 20 mM HEPES, pH 7.5, 100 mM KCl, and eluted with a linear KCl gradient from 0.1-1M KCl. Purified protein was snap-frozen in aliquots.

SDS-PAGE of reactions between HUH tags and ssDNA oligos: Unless otherwise noted, gel-shift assays were performed in HUH buffer; 50 mM HEPES pH 8, 50 mM NaCl, 1 mM $MgCl_2$ and 1 mM $MnCl_2$, incubated at 37° C. for 15 minutes unless otherwise noted, and quenched with 4×loading buffer. The reactions were analyzed by electrophoresis on 4-20% polyacrylamide gels and stained with either Coomassie Blue or Bio-Rad Stain-Free gels.

GFP targeting and analysis: GFP knockdown comparison of Cas9 and PCV-Cas9 was performed in a doxycycline inducible GFP cell line made by using In-Fusion HD Cloning (Clontech; Mountain View, Calif.) to insert GFP into the pLVX-TetOne vector (Clontech). This vector was then used to generate lentiviral particles. HT1080 cells (ATCC; Manassas, Va.) were then transduced with lentiviral particles for 48 hours and selected with puromycin in order to generate doxycycline-inducible GFP HT1080 cells. Cells were seeded to ~70% confluency in clear bottom 96-well plates. Ten (10) pmol of Cas9 or PCV2-Cas9 were treated with 50 pmol 3' Cy5 labeled PCV2 target oligo for 5 minutes in OPTI-MEM® (ThermoFisher) supplemented with 1 mM $MgCl_2$. Reactions were split in half and water or 10 pmol GFP single-guide RNA (sgRNA; including a trans-activating crRNA (tracrRNA) and the crRNA) was added for 10 minutes at room temperature. Reactions were split in half and 0.5 µl RNAiMAX (ThermoFisher) was added to half of the reactions for 15 minutes. RNP/liposome mixes were then added to cells in full-media minus antibiotics. Twelve (12) hours later, 1 µM doxycycline was added to wells. Cells were imaged using GFP and Cy5 channels on an EVOS-FL-AUTO 4-10 hours later. Analysis of GFP knockdown and Cy5 intensities was performed in ImageJ.

Cas9-PCV2 transfection and assaying scheme—transfection: Cas9-PCV2 ribonucleoproteins were reverse-transfected into HEK293T or U2-OS cells in 96-well format using RNAiMAX (ThermoFisher). The transfection mixture in OPTI-MEM® (ThermoFisher) contained 3-6 pmol Cas9 or Cas9-PCV protein pre-mixed with 3-6 pmol sgRNA for 10 minutes, followed by addition of 3-6 pmol ssODN containing PCV target sequence, 1.2 µl LIPOFECTAMINE™ reagent, and 0.1 mM $MgCl_2$. The mixture was incubated at room temperature for 5-20 minutes in a total volume of 100 µl. Cells were incubated for 48 hours at 37° C., 5% $CO_2$.

Cas9-PCV2 transfection and assaying scheme—luminescence assay: Forty-eight hours post-transfection, the cells were washed with PBS, trypsinized, and counted. The cells were centrifuged at 500×g for 5 minutes, and resuspended at $4 \times 10^5$ cells/mL in growth medium. Twenty thousand (20, 000) cells (25 µL) were transferred to a 96 half-well plate (Corning) along with 25 µL of the lytic detection reagent in the NanoGlo HiBiT lytic assay (Promega). The lytic detection reaction contained the luciferin substrate and recombinant protein (LgBiT) corresponding to the portion of split luciferase that will react with the HiBiT tag edited into the genome. The plate was incubated at room temperature for 15 minutes with shaking. Luminescence was assayed using an LMaxII luminometer (Molecular Devices; Sunnyvale, Calif.) with an integration time of 5 seconds.

Cas9-PCV2 transfection and assaying scheme—quantitative PCR: Genomic DNA from transfected cells was purified with the Purelink Genomic DNA mini-kit (ThermoFisher) per the manufacturer's instructions. Quantitative PCR was performed using 2× PowerUp SYBR Green Master Mix (Applied Biosystems; Foster City, Calif.). The GAPDH/HiBiT locus was amplified using GAPDH primers (Gapdh_F:CTCCCACCTTTCTCATCCAAG (SEQ ID NO:17) and Gapdh_R:ACATCACCCCTCTACCTCC (SEQ ID NO:18)) and HiBiT primers (HiBit_F:GAGACTGGCTCT-TAAAAAGTGC (SEQ ID NO:19) and HiBit_R: GCTAATCTTCTTGAACAGCCG (SEQ ID NO:20)). Unmodified gapdh was amplified using gapdh primers. Per reaction, 10 μL of mastermix was combined with 1 μM of each primer, 1 μL gDNA template, and 7 μL nuclease-free water. The two-step qPCR cycling conditions were initial denaturation at 95° C. for 3 minutes, followed by 40 cycles of 95° C. for 15 seconds and 58° C. for 35 seconds. Reactions were performed in triplicate. A method described elsewhere (Livak and Schmittgen; supra) was used to calculate the ratio between Cas9-PCV and Cas9 for HiBiT incorporation, using GAPDH as the reference.

Cas9-PCV2 transfection and assaying scheme—deep sequencing assay: A ~200 bp region encompassing a target locus in GAPDH or vinculin was PCR amplified using genomic DNA isolated from transfected HEK293T cells. The GAPDH locus was amplified using primers GAPDH_seq_F (CTGACAACTCTTTTCATCTTCT; SEQ ID NO:21) and GAPDH_seq_R (AAAGTGCAGGGTCTGGCG; SEQ ID NO:22). The vinculin locus was amplified with primers Vinculin_seq_F (ATGAGCTTGCTCCTC CCAAACC; SEQ ID NO:23) and Vinculin_seq_R (TCACTACTTACCTTGCTGGACC; SEQ ID NO:24). Amplicons were gel purified and subsequently ligated to barcoded adaptors. Deep sequencing was performed with an Illumina MiSeq with 2×150 bp paired-end reads (Genewiz Inc., Amplicon-EZ). Sequencing reads were analyzed using CRISPResso (see, e.g., Pinello et al., *Nat Biotechnol* 34:695-697, 2016).

Cas9-PCV2 transfection and assaying scheme—off-target analysis: Exonic off-target sites for the GAPDH sgRNA were identified using the CRISPR design tool (Zhang Lab, MIT). Regions surrounding the top four sites were amplified from genomic DNA and sequenced. Tracking of Indel by DEcomposition (TIDE) was employed to identify the indel frequency at each site, using a maximum indel size of 33 bp to account for HiBiT insertion.

Results

Figure 2:
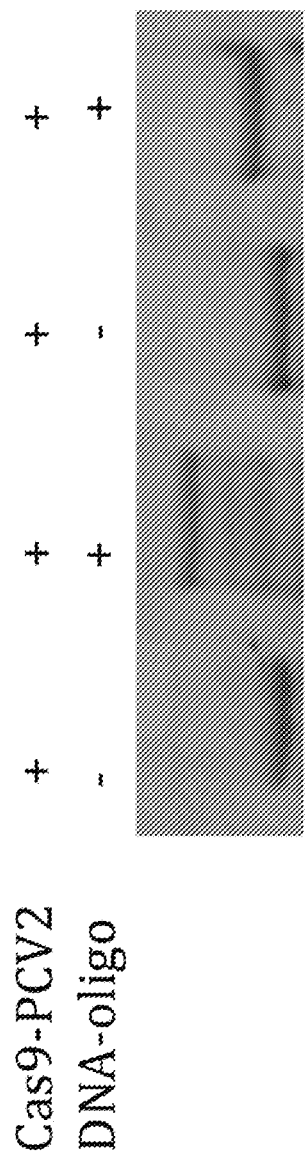
FIG. 2 is an image of an SDS-PAGE gel showing complexes formed between recombinant Cas9-PCV and single stranded DNAs containing the PCV2 target sequence, which forms covalent bonds with the PCV HUH tag, demonstrating in vitro activity. Cas9-PCV2 was reacted in the presence of 0.5 mM $Mg^{++}$ with a long (200 bp) ssODN (lane 2) and a shorter, ~50 bp oligonucleotide (lane 4). Lanes 2 and 4 show bands that run more slowly than the mock conditions (lanes 1 and 3), indicating that a covalent protein-DNA complex has formed and that the HUH tag functions properly when fused to Cas9.

HUH-Cas9 fusions were expressed in *E. coli* in fusion with an N-terminal His6-Sumo domain, and purified using affinity chromatography and cation exchange chromatography (FIG. 1). Reaction of recombinant PCV2-Cas9 with single stranded oligonucleotides bearing their target sequence in the presence of $Mn^{2+}/Mg^{2+}$ resulted in a characteristic covalent adduct, which ran more slowly on SDS-PAGE (FIG. 2). Guide RNA was prepared by in vitro transcription using a kit, or was purchased from IDT (San Jose, Calif.).

Figure 3B:
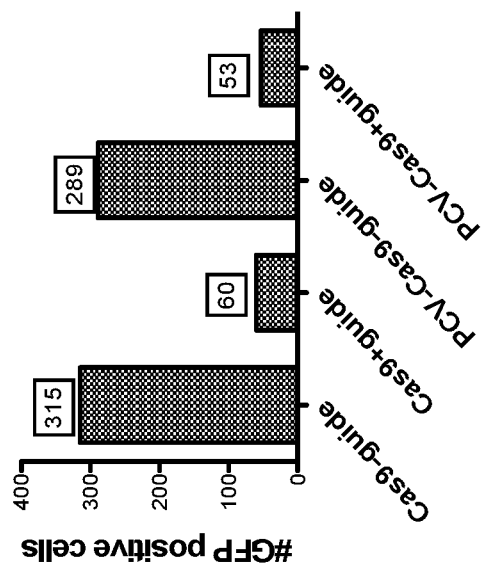
FIGS. 3A and 3B show the results of activity assays, demonstrating that Cas9 can cleave DNA efficiently when fused to an HUH tag. Cas9 or Cas9-PCV was complexed with (1) a gRNA targeted to the GFP locus and designed to interrupt the coding frame of GFP, thus silencing its fluorescence, and (2) an oligonucleotide bearing the PCV2 target sequence conjugated to Cy5 for visualization. The ribonucleoproteins (RNPs) were reverse transfected into an HT1080 cell line stably encoding an inducible GFP. After 12 hours, doxycycline was added to induce GFP expression. When the Cas9 RNP correctly targeted the GFP locus via its gRNA, double strand breaks occurred, resulting in less GFP fluorescence (FIG. 3A, right panels). GFP fluorescence was read on an EVOS FL-AUTO microscope, and GFP positive cells quantitated using ImageJ. Results are plotted in FIG. 3B, showing a similar loss of GFP fluorescence for both Cas9 and Cas9-PCV when the GFP targeting gRNA was present, demonstrating that Cas9 activity was not affected when the endonuclease was fused to the PCV HUH tag.
Figure 3A:
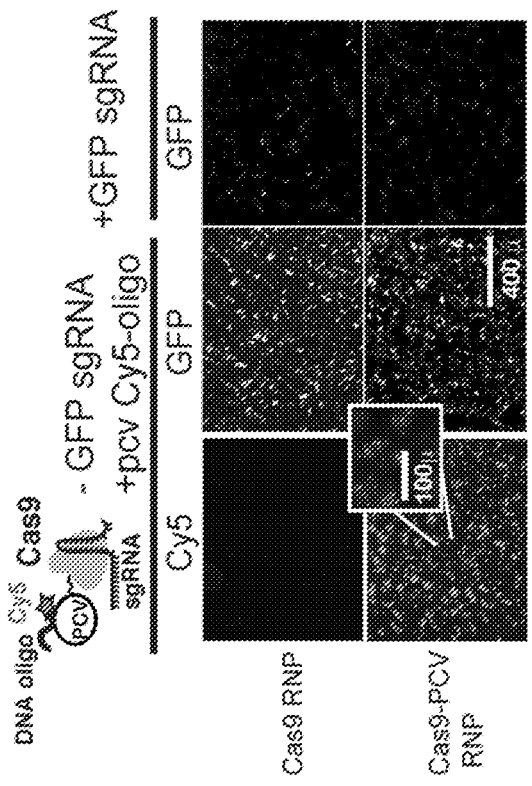

To determine if the Cas9-PCV fusion could induce double stranded breaks as efficiently as Cas9, Cas9 or Cas9-PCV RNPs with a gRNA targeting GFP were delivered to an inducible GFP HCT119 cell line. If Cas9 induced DSBs, the GFP intensity would be decreased. A cationic lipid (LIPOFECTAMINE™ RNAiMAX; ThermoFisher Scientific) was used to deliver 1 pmol Cas9 or Cas9-HUH and 1 pmol GFP gRNA to HCT116 cells stably expressing an inducible GFP. Twelve hours later, GFP expression was induced with doxycycline. After another 12 hours, GFP fluorescence was measured using an EVOS-FL-AUTO fluorescent microscope (ThermoFisher Scientific), and GFP intensity was quantitated using ImageJ. Cas9 and Cas9-PCV caused a similar reduction in GFP fluorescence as compared to the reaction in the absence of the targeting gRNA (FIGS. 3A and 3B).

Figure 4:
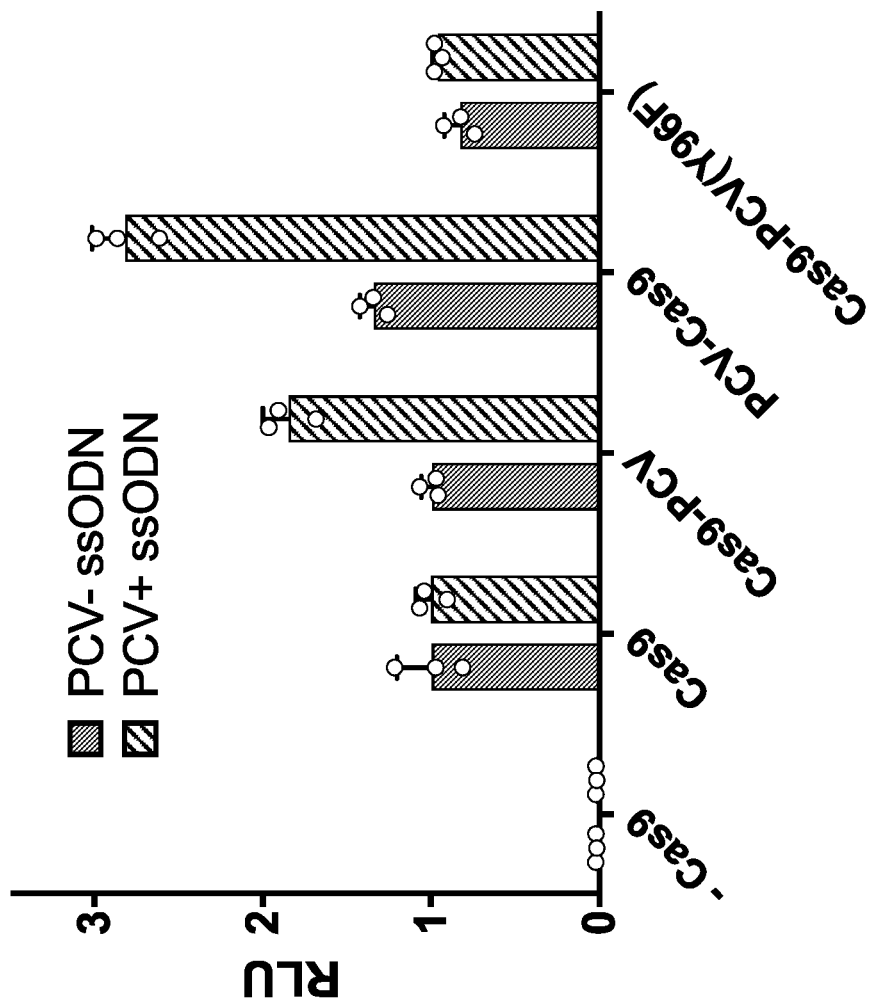
FIG. 4 is a graph showing that tethering of a ssODN to a Cas9-gRNA RNP enhances HDR efficiency. Cas9 was compared to Cas9-PCV fusions for its efficiency in utilizing HDR to incorporate a sequence encoding an 11 amino acid peptide into the endogenous GAPDH gene in HEK293T cells. The 11 amino acid peptide was a split-luciferase tag (e.g., NanoGlo HiBiT lytic assay) that luminesces when the remaining portion of luciferase and luciferase substrate are added (Promega; Madison, Wis.). The Cas9-PCV fusions contained PCV fused either to the amino terminus (PCV-Cas9) or the carboxyl terminus (Cas9-PCV) of Cas9. A Cas9-PCV mutant (Cas9-PCV(Y96F)) that cannot covalently link to DNA also was tested. Cas9 or the Cas9-PCV fusions were complexed with a gRNA targeted to the 3' end of GAPDH and reacted with a 200 bp ssODN either lacking (PCV-ssODN) or containing (PCV+ssODN) a 5' PCV target sequence to allow covalent tethering to the HUH tag. The complexes were transfected into cells using the cationic lipid LIPOFECTAMINE™ RNAiMAX (ThermoFisher Scientific; Waltham, Mass.). After 48 hours, the cells were lysed and luciferase reagents were added. Bioluminescence was read on a luminometer in relative light units (RLU).

To determine if tethering of the donor DNA, allowing Cas9, sgRNA, and donor DNA to be delivered as a single complex, has the potential to improve HDR, gene editing was used to insert a small peptide tag at the C-terminus of GAPDH. This peptide tag was part of a split-luciferase system developed by Promega; when the small peptide is incorporated in-frame into GAPDH and reacted with the other portion of the split-luciferase system plus the luciferase substrate, gene-editing can be detected by measuring luminescence. Briefly, a cationic lipid (LIPOFECTAMINE™ CRISPRMAX™; ThermoFisher Scientific) was used to deliver recombinant Cas9 or Cas9-PCV fusions along with sgRNA targeting the C-terminus of GAPDH (purchased from IDT), with or without ssODNs containing the peptide-tag and ~50 bp homology arms± the PCV2 targeting sequence into HEK293T cells. After 48 hours, the cells were lysed, the split-luciferase and luciferase substrate were added, and luminescence was measured. It was consistently observed that the Cas9-PCV fusion coupled with the ssODN containing the PCV2 target sequence to allow covalent coupling resulted in higher levels of luminescence (FIG. 4). Moreover, mutation of the catalytic tyrosine of PCV2, which prevents covalent attachment of the DNA, abrogated the enhancement in luminescence (see, the far right columns of FIG. 4).

Figure 5A:
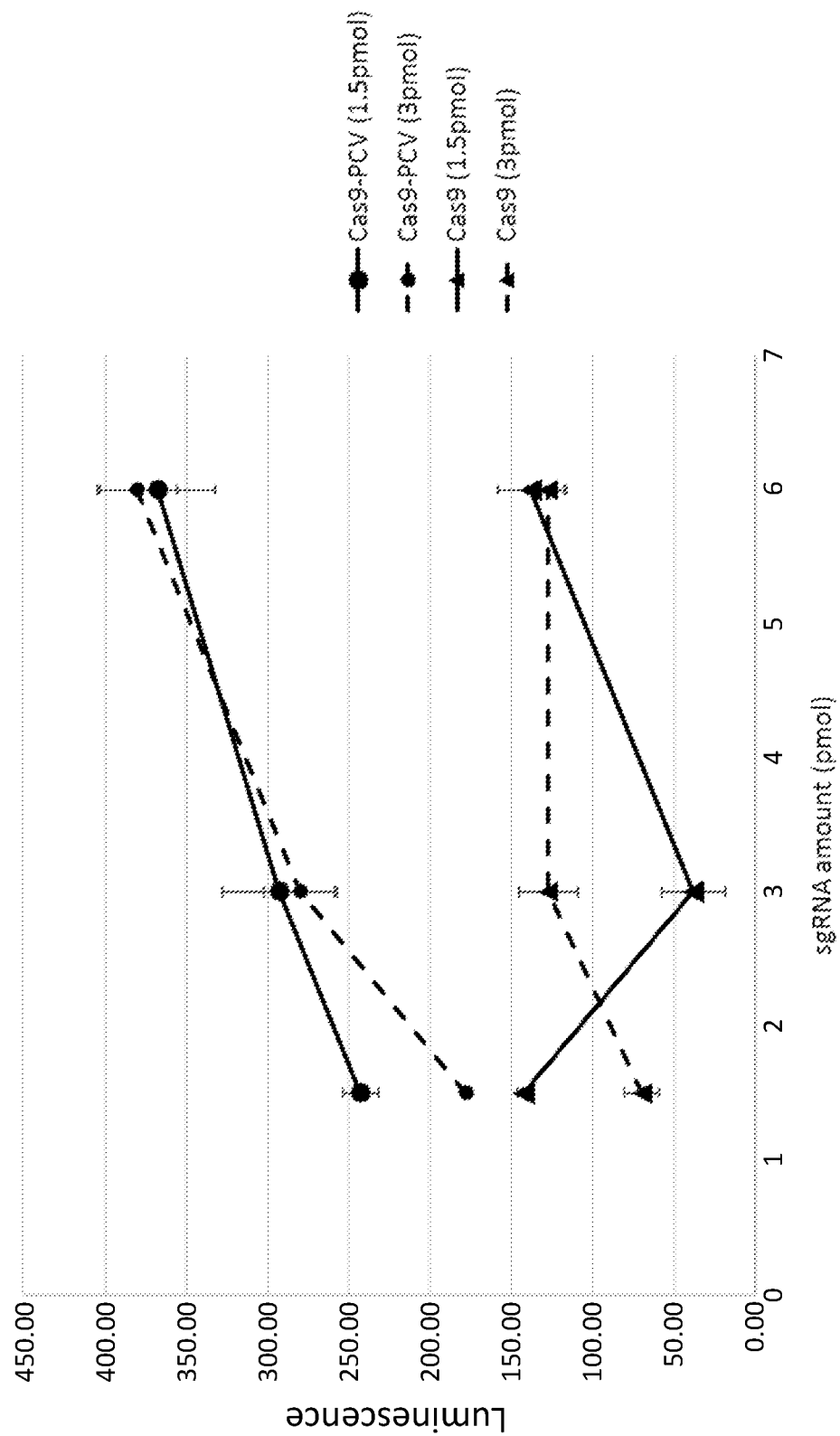
FIGS. 5A and 5B are graphs plotting luciferase activity obtained when the amounts of the RNP components (the Cas9 or Cas9-PCV and the gRNA) were varied. An enhancement of HiBIT incorporation (represented as RLU) was observed when Cas9-PCV was used as compared to Cas9, regardless of concentration. These data indicate that the enhancement is not simply a result of errors in measuring concentrations of the two different proteins.
Figure 5B:
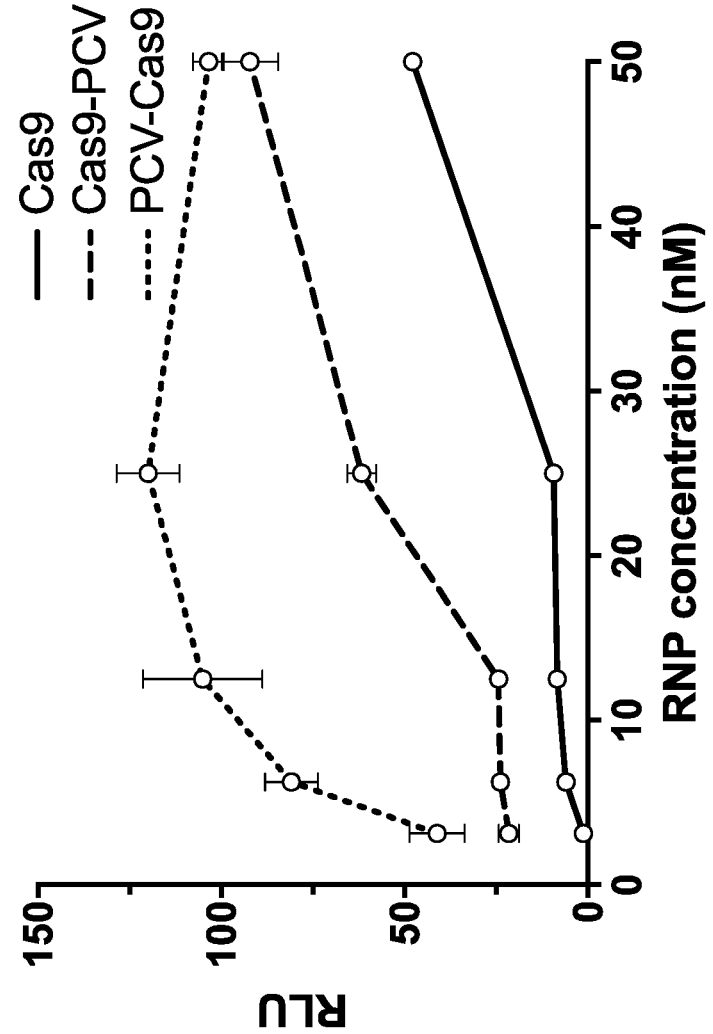

Further experiments were conducted to evaluate the effects of varying the amounts of the RNP components (the Cas9 or Cas9-PCV and the gRNA). As shown in FIGS. 5A and 5B, HiBIT incorporation (represented as RLU) was enhanced when Cas9-PCV fusions were used, as compared to Cas9 alone, regardless of concentration. Thus, the enhancement was not simply a result of errors in measuring concentrations of the two different proteins.

Figure 6A:
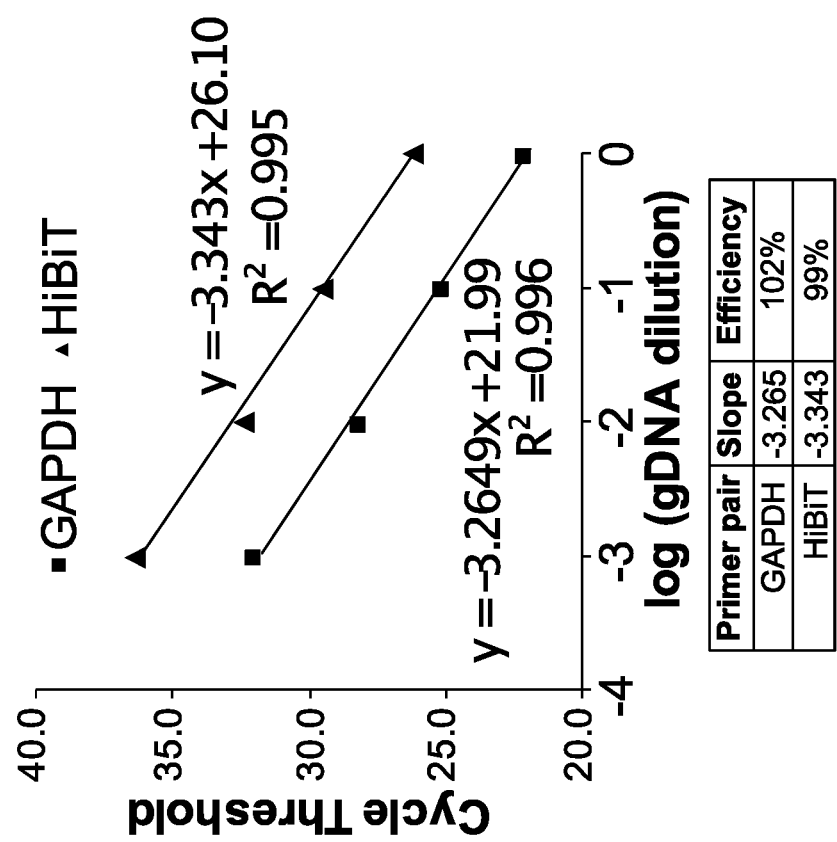
Figure 6C:
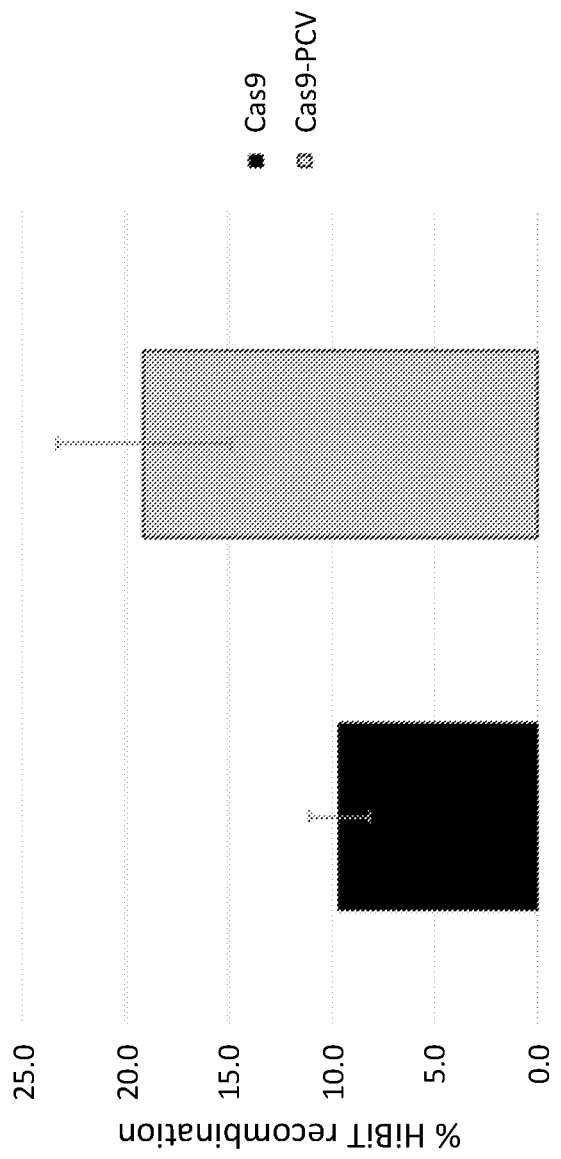

DNA analyses also showed that covalent tethering of the donor DNA to the CRISPR/Cas9 complex enhanced HDR. Quantitative polymerase chain reaction (also referred to as real-time PCR) was performed on cell lysates with two sets of primers—a GAPDH set that annealed to unmodified GAPDH, and a HiBIT set that annealed to luciferase-tag modified GAPDH. The amplification efficiencies of the primers were equivalent (FIG. 6A), demonstrating that the cycle threshold values could be compared. Cycle threshold times are provided in FIG. 6B for triplicate measurements for both sets of primers for PCV or PCV-Cas9. The cycle threshold values were used to calculate the relative incorporation of HiBIT into GAPDH, revealing a two-fold enhancement of HDR efficiency (FIG. 6C) and demonstrating that covalent tethering of the donor DNA to Cas9-PCV enhanced HDR.

Figure 7A:
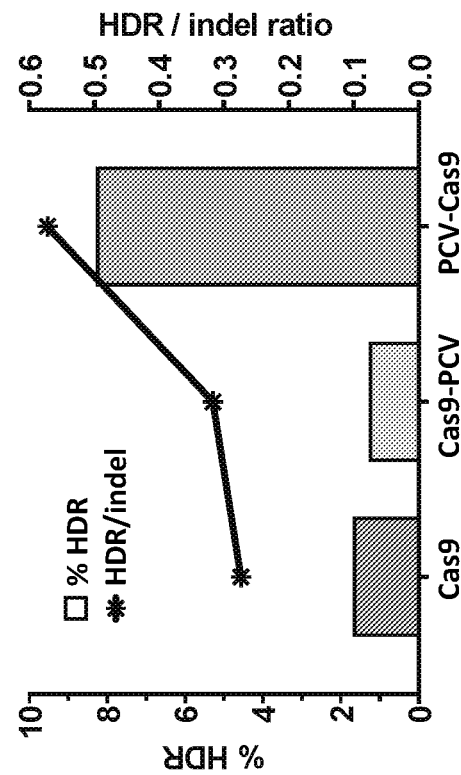
FIGS. 7A and 7B are a graphs plotting absolute HDR efficiencies summarized from deep sequencing results at two different target loci. Cas9 or Cas9-PCV was used to introduce a 33 bp edit in either the GAPDH gene (FIG. 7A) or the vinculin gene (FIG. 7B). The % HDR corresponds to the percentage of sequences that contained the 33 bp insertion. The HDR/indel ratio represents the precise gene editing rate. The fusion of PCV to Cas9 increased both the absolute gene editing efficiency and the precise gene editing ratio.
Figure 7B:
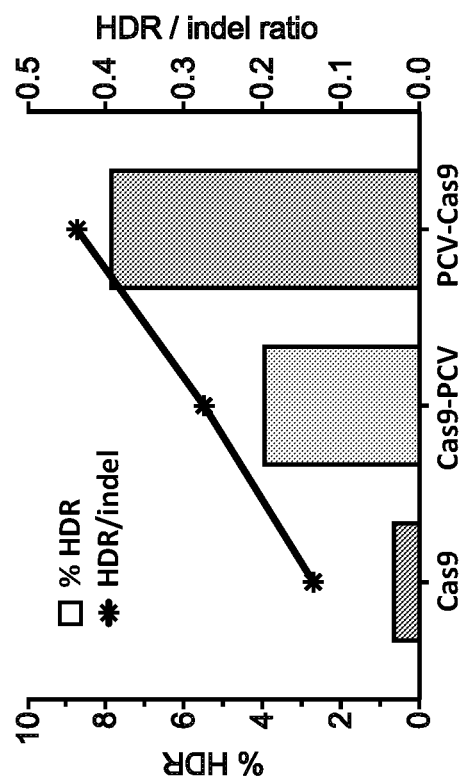

Absolute HDR efficiencies were summarized from deep sequencing results at two different target loci. Cas9 or Cas9-PCV was used to introduce a 33 bp edit in either the GAPDH gene (FIG. 7A) or the vinculin gene (FIG. 7B), and the % HDR was determined. The HDR/indel ratio representing the precise gene editing rate also was determined. These studies showed that fusion of PCV to Cas9 increased both the absolute gene editing efficiency and the precise gene editing ratio.

Figure 8:
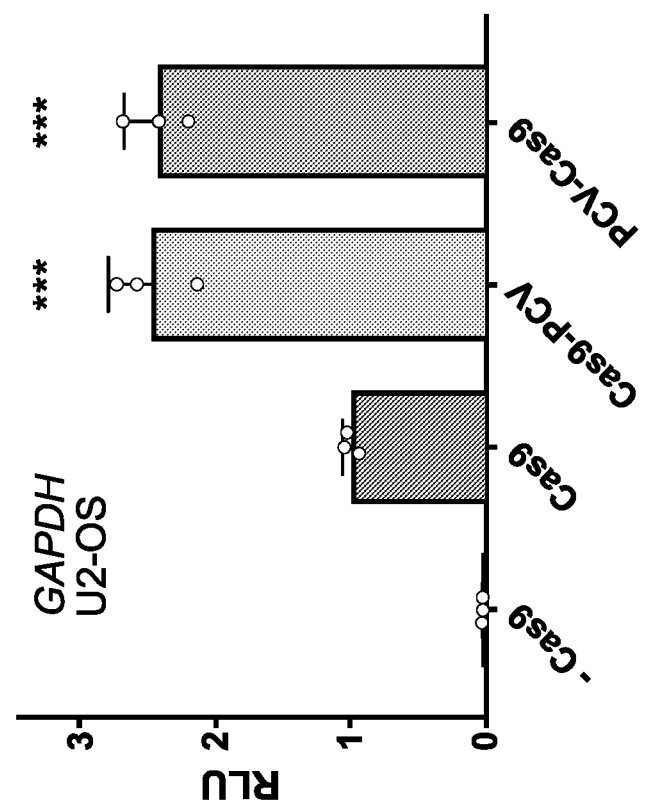
FIG. 8 is a graph plotting the results of inserting the HiBiT tag in U2-OS cells. Luciferase activity was read after targeting the GAPDH locus in U2-OS cells. A significant increase in HDR efficiency was observed when using the Cas9-PCV fusions. Significance was calculated using 2-tailed Student's t test: ***P<0.001.

In additional studies, the HiBiT tag was inserted into the GAPDH gene in U2-OS osteosarcoma cells, and luciferase activity was measured. A significant increase in HDR efficiency was observed when the Cas9-PCV fusions were used, as compared to Cas9 along (FIG. 8; P<0.001).

Figure 9:
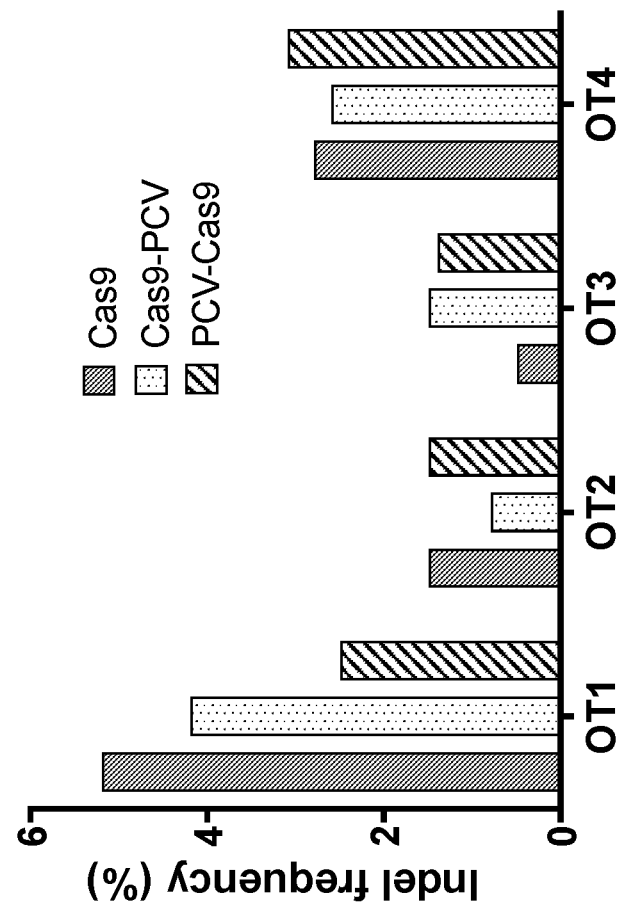
FIG. 9 is a graph plotting the editing rates at the top four exonic off-target (OT) sites of the GAPDH sgRNA. Tracking of Insertion/Deletion by DEcompostion (TIDE) analysis revealed no increase in off-targeting effects due to covalent tethering of the ssODN.

Finally, editing rates at the top four exonic off-target (OT) sites of the GAPDH sgRNA were measured using Tracking of Insertion/Deletion by DEcompostion (TIDE) analysis. No increase in off-targeting effects due to covalent tethering of the ssODN was observed (FIG. 9).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for modifying the genetic material of a cell, comprising introducing into the cell a ribonucleic acid protein (RNP) complex, wherein the RNP complex comprises:
   (a) a polypeptide comprising a Cas9 endonuclease and an HUH tag;
   (b) a guide RNA targeted to a selected sequence in the genome of the cell; and
   (c) a donor DNA containing a single-stranded target sequence that can specifically interact with the HUH tag;
   wherein, after said introducing, the guide RNA directs the RNP complex to the selected sequence, the Cas9 endonuclease induces a nick or a double strand break at or near the selected sequence, and the donor DNA is inserted at the double stranded break, and wherein covalent tethering of the donor DNA to the Cas9-HUH/gRNA complex enhances HDR compared to Cas9 alone.

2. The method of claim 1, wherein the polypeptide comprises a linker between the Cas9 endonuclease and the HUH tag.

3. The method of claim 1, wherein the HUH tag is at the N-terminus of the Cas9 endonuclease or at the C-terminus of the Cas9 endonuclease.

4. The method of claim 1, wherein the Cas9 endonuclease comprises one or more mutations as compared to the Cas9 endonuclease having the amino acid sequence set forth in SEQ ID NO:14 or SEQ ID NO:15.

5. The method of claim 1, comprising introducing the RNP complex into the cell using a cationic lipid, electroporation, or injection.

6. The method of claim 1, wherein the RNP complex is attached to an antibody, a nanobody, or an ScFv that binds to a cell-surface antigen of the cell.

7. The method of claim 1, wherein the RNP complex is attached to a gold nanoparticle, or is attached to a cell-penetrating polypeptide.

* * * * *